United States Patent
Trujillo et al.

(10) Patent No.: US 10,548,950 B2
(45) Date of Patent: Feb. 4, 2020

(54) IRISIN-RELATED CANCER TREATMENTS

(71) Applicant: STC.UNM, Albuquerque, NM (US)

(72) Inventors: Kristina Trujillo, Placitas, NM (US);
Nicholas Patrick Gannon, Albuquerque, NM (US); Roger Alan Vaughan, High Point, NC (US)

( * ) Notice: Subject to any disclaimer, the term of this patent is extended or adjusted under 35 U.S.C. 154(b) by 2 days.

(21) Appl. No.: 15/528,348

(22) PCT Filed: Nov. 18, 2015

(86) PCT No.: PCT/US2015/061349
§ 371 (c)(1),
(2) Date: May 19, 2017

(87) PCT Pub. No.: WO2016/081603
PCT Pub. Date: May 26, 2016

(65) Prior Publication Data
US 2017/0312339 A1    Nov. 2, 2017

Related U.S. Application Data

(60) Provisional application No. 62/082,460, filed on Nov. 20, 2014.

(51) Int. Cl.
| | | |
|---|---|---|
| A61K 39/00 | (2006.01) | |
| A61K 38/22 | (2006.01) | |
| A61K 45/06 | (2006.01) | |
| A61K 31/704 | (2006.01) | |
| A61K 31/337 | (2006.01) | |

(52) U.S. Cl.
CPC ............ *A61K 38/22* (2013.01); *A61K 31/337* (2013.01); *A61K 31/704* (2013.01); *A61K 45/06* (2013.01)

(58) Field of Classification Search
None
See application file for complete search history.

(56) References Cited

PUBLICATIONS

Gonnon et al ( Int J Cancer. Feb. 15, 2015;136(4):E197-202. doi: 10.1002/ijc.29142. Epub Aug. 30, 2014. (Year: 2014).*
Gannon et al, (Int J Cancer 136:E197-202, online published Aug. 30, 2014, IDS filed May 19, 2017, item #1. (Year: 2014).*
Metabolism Clinical and Experimental 63:188-193, 2014 (Year: 2014).*
Gannon NP et al. Effects of the exercise-inducible myokine irisin on malignant and non-malignant breast epithelial cell behavior in vitro. Int J Cancer Feb. 15, 2015; 136(4):E197-202(abstract), [online], doi: 10,1002/ijc.29142. Epub Aug. 30, 2014.
Lee P et al. Irisin andFGF21 are cold-induced endocrine activators of brown fat function in humans. Cell Metab, Feb. 4, 2014; 19(2):302-9, (abstract), [online], doi: 10.1016/j.cmet.2013.12.017.
Gouni-Berthold I et al. Effects of lipid-lowering drugs on irisin in human subjects in vivo and in human skeletal muscle cells exvivo. PLoS One, Sep. 2, 2013; 8(9):e72858, (abstract), [online], doi: 10.1371/journal.pone.0072858. eCollection 2013.
Anwar MA et al. Colorectal and Prostate Cancer Risk in Diabetes: Metformin, an Actor behind the Scene. J Cancer, Oct. 9, 2014;5(9):736-44, (abstract), [online], doi: 10.7150/jca.9726. eCollection 2014.
Vector Map: pDONR223, Human and Mouse ORFeome Collaboration Clones, DNAFORM, 2009, pp. 1-4.
Database UniProtKB-U6DAJ4 (U6DAJ4_NEOVI), FNDC5, Jan. 22, 2014.
Erickson P.H. Irisin and FNDC5 in retrospect. An exercise hormone or a transmembrane receptor? Adipocyte, 2013, 2:4, 289-293.

* cited by examiner

*Primary Examiner* — Lei Yao
(74) *Attorney, Agent, or Firm* — Henry D. Coleman; R. Neil Sudol

(57) ABSTRACT

In one embodiment, the invention provides methods of treating or preventing cancer, in particular aspects breast and/or prostate cancer, by administering to a subject in need thereof a therapeutically-effective amount of irisin and, optionally, one or more adjuvant therapies (e.g. synergistic co-administration of an additional anti-cancer agent or chemotherapy). Related pharmaceutical compositions, assays and kits are also provided.

31 Claims, 17 Drawing Sheets

Specification includes a Sequence Listing.

IRISIN-RELATED CANCER TREATMENTS

RELATED APPLICATIONS

This application is a United States national phase patent application based upon international patent application number PCT/US2015/061349 filed Nov. 18, 2015, which claims the benefit of priority of U.S. provisional application No. 62/082,460, filed Nov. 20, 2014, entitled "Irisin-Related Breast Cancer Treatments", the entire contents of which are incorporated by reference herein.

FEDERAL FUNDING

This invention was made with government support under grant P20 GM103451 awarded by the awarded by NIH. The government has certain rights in the invention.

FIELD OF THE INVENTION

In one embodiment, the invention provides methods of treating or preventing breast and other cancers, including prostate cancer by administering to a subject in need thereof a therapeutically-effective amount of irisin and, optionally, one or more adjuvant therapies (e.g. synergistic co-administration of an additional anti-cancer agent or chemotherapy, radiation and the like). Related pharmaceutical compositions, assays and kits are also provided.

BACKGROUND OF THE INVENTION

Exercise provides many health benefits for metabolic diseases including obesity, type 2 diabetes mellitus, cardiovascular disease, and cancer.[1-3] Previous studies have reported a 30-40% reduction of breast cancer risk in women who exercise regularly which appears to function in a dose dependent fashion.[4] Moreover, women with breast cancer have an improved survival rate if they participate in regular exercise.[5-8] While the link between exercise and weight loss is well established, the mechanisms by which exercise decreases rates of cancer and improves survival are not well understood.

Irisin, a recently identified myokine believed to be released from skeletal muscle following exercise, is implicated as a potential therapeutic in a variety of metabolic diseases.[9] Circulating levels of irisin appear to be reduced among type II diabetes and chronic kidney disease populations, while unaffected among anorexic populations.[10-12] The mechanism of irisin secretion remains controversial, although it appears circulating irisin levels are correlated with lean body mass and may be elevated by exercise or cold exposure.[9, 13, 14] Irisin has gained much interest because of its ability to stimulate metabolism and mitochondrial biogenesis in adipocytes and myocytes.[9, 15] In the context of cancer, circulating concentrations of irisin among cancer patients remains unknown, although data suggest irisin treatment of select obesity related cancer cell lines does not alter viability.[16]

PGC1-α overexpression in muscle stimulates an increase in expression of fibronectin type III domain containing protein 5 (FNDC5), a membrane protein that is cleaved and secreted as irisin. A prior study has shown that FNDC5 induces browning of subcutaneous fat in mice and mediates beneficial effects of exercise on metabolism. Hu, et al., "FNDC5 and irisin in humans: I. Predictors of circulating concentrations in serum and plasma and II. mRNA expression and circulating concentrations in response to weight loss and exercise." *Metabolism,* 2012 December; 61(12): 1725-38. Irisin can act on cells (e.g., white adipose cells) in culture and in vivo to stimulate UCP1 expression and a broad program of brown fat-like development. Irisin is induced with exercise in both mouse and man, and mildly increased Irisin blood levels cause an increase in energy expenditure in mice with no change in movement or food intake. This results in improvement in metabolic disorders (e.g., obesity, insulin resistance, and glucose homeostasis). See U.S. Patent Application Document No. 20130074199.

Metformin promotes irisin release from murine skeletal muscle into blood, independently of AMPK pathway activation. Li, et al., "Metformin promotes irisin release from murine skeletal muscle into blood, independently of AMPK pathway activation", *Acta Physiol. (Oxf.)* 2014 Nov. 10. (epub).

Because of irisin's potent metabolic effects on several tissue types, it is conceivable that irisin may possess the ability to alter malignant characteristics similar to other myokines.[17] We hypothesize that irisin, along with other myokines and circulating factors, affect the development and aggressiveness of breast cancer. The skeletal muscle secretory factors such as interleukin 6 (IL-6) and tumor necrosis factor alpha (TNF-α) have previously been shown to alter breast cancer proliferation, and aggressiveness.[18, 19] While irisin has been explored in other tissue types with implications for metabolic disease, to our knowledge this is the first attempt to characterize the molecular effects of irisin in breast cancer.

Turning to prostate cancer, physical activity is beneficial for a variety of pathologies, and is regarded as a mechanism by which the development and progression of said pathologies can be alleviated or lessened. Increased body weight and fat is linked with cancer risk, and well-controlled body weight appears to be positively influential in cancer prevention (1-3, see second set set of references). It is believed that modifiable lifestyle changes and physical activity decrease the risk of prostate cancer development (4,5). In an analysis of 10,258 men, the Prostate Cancer Prevention Trial concluded that obesity (BMI≥30) is closely associated with increased risk of high-grade prostate cancer, but a decreased risk of low-grade prostate cancer (6). Moreover, acute exercise (brisk walking) a few hours per week is associated with lower mortality, post-diagnosis, in men with prostate cancer, and may inhibit or delay further progression of localized prostate cancer (7,8).

The surface of skeletal muscle expresses the trans-membrane protein, fibronectin type III domain-containing protein 5 (FNDC5), whose expression is tightly controlled by peroxisome proliferator-activated receptor gamma coactivator 1-alpha (PGC-1α) (9). In a yet-to-be-identified fashion, the C-terminus of FNDC5 is truncated during skeletal muscle contraction (exercise and shivering), and a 112 amino acid truncated portion is released into circulation, termed irisin, after the Greek messenger goddess "Iris." The myokine is proposed to exist biologically and function as a dimer glycosylated at residues Asn7 and Asn52, eliciting its effects after binding to an unknown ligand-specific cell surface receptor (10,11). Irisin is thought to possibly represent a therapeutic agent for obesity due to its role as a potent stimulator of metabolism in skeletal muscle through increased mitochondrial density, and browning of adipose through upregulation of uncoupling protein 1 (UPC1), dissipating cellular energy as heat via thermogenesis (9,12). It has previously been shown that irisin levels are negatively associated with age, and positively associated with BMI, muscle mass body-cell mass, and fat-free mass, and found at higher levels in lean males over obese females, but not lean females or obese males (13). It has repeatedly been shown that acute bouts of exercise greatly elevate serum irisin levels shortly following exercise, while long-term endurance training regimens do not enhance release or total levels (13-15). While irisin is believed to be beneficial, a large body of controversial evidence exists in regards to the stimulation of irisin release, and levels in select populations. Irisin levels have been shown to be decreased in type 2 diabetic individuals, increased and decreased in individuals with metabolic syndrome, and increased in obese individuals (16-21).

Exercise stimulates the release of circulating factors from muscle and adipose that influence and protect the advancement of select pathologies, some of which and their mechanisms of action remain elusive. Because skeletal muscle is involved in endocrine cross-talk with other tissues and cancers, we hypothesized that irisin may function similarly to other secretory factors released following exercise and provide benefit for prostate cancer. Our group has previously demonstrated that irisin, without post-translational modifications, reduced malignant breast epithelial cell number, migration and viability, differentially without affecting non-malignant cells (22). Moreover, non-modified irisin enhanced cell sensitivity and the cytotoxic effect of doxorubicin, while decreasing cellular uptake, lowering the effective killing dose approximately one hundred-fold (22). Interestingly, our group also found that non-modified irisin decreased activation of nuclear factor kappa-light-chain-enhancer of activated B cells (NFκB), possibly supporting the notion that irisin may function as an anti-inflammatory cytokine to counter pro-inflammatory cytokines that potentiate cancer metastasis and aggressive development (22). Because we have previously shown that non-modified irisin had profound effects on a hormone/endocrine-related cancer (breast) and because prostate cancer is also sensitive to endocrine axes, we hypothesized that non-modified irisin may have similar effects in prostate cancer to those in breast cancer. The objective of the present study was to examine the effects of irisin on locally advanced and invasive prostate cancer aggressiveness and characteristics, along with its role as a potential therapeutic as an adjuvant treatment with a commonly used chemotherapy. Lastly, we sought to determine whether or not irisin had activity as a potential prostate cancer therapy. While the effects of irisin have been assessed in breast cancer, obesity related cancers, and other pathologies, to our knowledge these data are the first documented in prostate cancer.

SUMMARY OF THE INVENTION

We evaluated the effects of various concentrations of irisin (with and without post-translational modifications) on malignant and non-malignant breast epithelial cell proliferation, migration, and viability. Irisin significantly decreased proliferation, migration, and viability in malignant MDA-MB-231 cells, without affecting non-malignant MCF-10a cells. Moreover, irisin enhanced the cytotoxic effect of doxorubicin (Dox) when added to a wide spectrum of irisin concentrations in the malignant cell type (with simultaneous reduction in Dox uptake), which was not observed in non-malignant MCF-10a cells. Additionally, we found that irisin decreases malignant cell viability in part through stimulation of caspase activity leading to apoptotic death. Interestingly, we found that irisin does not appear to function through NFκB, as do other myokines such as tumor necrosis factor alpha (TNF-α). Our observations indicate that irisin offers therapeutic benefits for cancer prevention, including breast cancer prevention and treatment likely through induction of apoptotic cell death and/or through enhanced tumor sensitivity to common antineoplastic agents such as Dox.

Significantly, we demonstrate that irisin may allow for reduced doses of common antineoplastics due to increased tumor sensitivity, thereby improving patient tolerance and prognosis.

In one embodiment, the invention provides a method of treating a subject who suffers from, or who is at risk of developing, a cancer, especially including a germ-line cancer, often breast cancer or prostate, the method comprising administering to the subject a therapeutically effective amount of irisin, including a pharmaceutically acceptable salt thereof and/or a composition that increases plasma or serum levels of irisin (e.g. metformin, a statin or a vector which contains a nucleic acid encoding FNDC5 and which upregulates muscle cell FNDC5 expression).

In some embodiments, the subject suffers from a form of resistant cancer, such as refractory breast cancer, e.g. where the subject has developed an acquired anti-estrogen resistance or a recurrent cancer where the subject has developed a resistance to chemotherapy. In other embodiments, the subject with breast cancer exhibits an intrinsic resistance to anti-estrogen and anti-HER2 therapies. In other instances the subject is at risk for or has developed prostate cancer or another cancer, including a cancer, especially a prostate cancer which is resistant to chemotherapy. The therapeutic methods of the present invention may be used to inhibit, treat or reduce the likelihood of metastatic cancers, chemotherapy resistant cancers, including recurrent cancers, especially breast and/or prostate cancer.

In certain embodiments, the subject is co-administered (1) a therapeutically effective amount of irisin, and/or a composition that increases plasma or serum levels of irisin (e.g. metformin, a statin or a vector which contains a nucleic acid encoding FNDC5 and which upregulates muscle cell FNDC5 expression), and (2) one or more therapeutic agents selected from the group consisting of a chemotherapeutic agent, a HER antibody, an antibody directed against a tumor associated antigen, an anti-hormonal compound, a cardioprotectant, a cytokine, an EGFR-targeted drug, an anti-angiogenic agent, a tyrosine kinase inhibitor, a COX inhibitor, a non-steroidal anti-inflammatory drug, a farnesyl transferase inhibitor, an antibody that binds oncofetal protein CA 125, HER2 vaccine, HER targeting therapy, Raf or ras inhibitor, doxorubicin (e.g. liposomal doxorubicin), topotecan, taxane, a dual tyrosine kinase inhibitor, TLK286 and EMD-7200.

In other embodiments, the subject is a HER2 positive metastatic breast cancer patient and is administered a therapeutically amount of irisin, including a pharmaceutically acceptable salt thereof and/or a composition that increases plasma or serum levels of irisin (e.g. metformin, a statin or a vector which contains a nucleic acid encoding FNDC5 and which upregulates muscle cell FNDC5 expression), and at least one additional anti-cancer agent selected from the group consisting of a growth inhibitory HER2 antibody (e.g. pertuzumab or trastuzumab), a HER2 dimerization inhibitor antibody and a taxane.

In certain embodiments, the subject is administered human recombinant non-modified irisin (INM) or human recombinant modified and active (glycosylated) irisin (IM).

In a preferred embodiment, the invention provides a method of treating a subject who suffers from a cancer, especially breast or prostate cancer, the method comprising administering to the subject a therapeutically-effective amount of irisin and/or a composition that increases plasma or serum levels of irisin (e.g. metformin, a statin or a vector which contains a nucleic acid encoding FNDC5 and which upregulates muscle cell FNDC5 expression) and doxorubicin and/or another chemotherapeutic agents as otherwise disclosed herein.

In embodiments directed to the treatment and/or prevention of cancer, especially breast or prostate cancer, the irisin and/or composition which increase the plasm or serum levels of irisin (which may further include the administration of another anticancer compound as described herein), alternative therapies may be used in including androgen deprivation (for prostate cancer), radiation therapy, hormonal therapy, proton therapy, cryosurgery, and/or high intensity focused ultrasound (HIFU) is used, depending upon clinical assessments and treatment goals.

In embodiments directed to the treatment of prostate cancer, in addition to the treatments identified above, at least one antiandrogen agent and/or an enlarged prostate agent may be included along with the other compounds/compositions administered to the subject or patient. Preferred antiandrogen agents are selected from the group consisting of flutamide, bicalutamide, nilutamide, cyproterone aceate, ketoconazole, aminoglutethimide, abarelix, leuprolide, goserelin, triptorelin, buserelin, abiraterone acetate, sorafenib and mixtures thereof. Preferred enlarged prostate agents for use in the present invention include, for example, eulexin, flutamide, goserelin, leuprolide, lupron, nilandron, nilutamide, zoladex and mixtures thereof.

In another embodiment, the invention provides a method of improving the prognosis of a subject who suffers from cancer, especially breast or prostate cancer, the method comprising administering to the subject a therapeutically effective amount of irisin and/or a composition that increases plasma or serum levels of irisin (e.g. metformin, a statin or a vector which contains a nucleic acid encoding FNDC5 and which upregulates muscle cell FNDC5 expression), thereby increasing the subject's tolerance to adjuvant cancer therapies (which include, in preferred embodiments, the co-administration of doxorubicin and/or another chemotherapeutic agent).

In another embodiment, the invention provides a pharmaceutical composition comprising:
(a) a therapeutically effective amount of irisin and/or a composition that increases plasma or serum levels of irisin (e.g. metformin, a statin or a vector which contains a nucleic acid encoding FNDC5 and which upregulates muscle cell FNDC5 expression);
(b) optionally, a therapeutically effective amount of one or more anti-cancer agents selected from the group consisting of at least one additional anticancer agent as otherwise described herein, preferably a chemotherapeutic agent, a HER antibody, an antibody directed against a tumor associated antigen, an anti-hormonal compound, a cardioprotectant, a cytokine, an EGFR-targeted drug, an anti-angiogenic agent, a tyrosine kinase inhibitor, a COX inhibitor, a non-steroidal anti-inflammatory drug, a farnesyl transferase inhibitor, an antibody that binds oncofetal protein CA 125, HER2 vaccine, HER targeting therapy, Raf or ras inhibitor, doxorubicin (e.g. liposomal doxorubicin), topotecan, taxane, a dual tyrosine kinase inhibitor, TLK286 and EMD-7200; and/or
(c) optionally, at least one antiandrogen compound, preferably selected from the group consisting of flutamide, bicalutamide, nilutamide, cyproterone acetate, ketoconazole, aminoglutethimide, abarelix, leuprolide, goserelin, triptorelin, buserelin, abiraterone acetate, sorafenib and mixtures thereof and/or
(d) optionally, at least one enlarged prostate agent, preferably selected from the group consisting of eulexin, flutamide, goserelin, leuprolide, lupron, nilandron, nilutamide, zoladex and mixtures thereof; and/or
(e) optionally, a pharmaceutically-acceptable carrier, additive and/or excipient.

In still another embodiment, the invention provides a method of treating a subject who suffers from, or who is at risk of developing cancer, especially including breast or prostate cancer, the method comprising subjecting the subject to stimuli (e.g. one or more periods of acute or chronic exercise, and/or to one or more periods of cold exposure) sufficient to induce shivering or non-shivering thermogenesis. This method may be used alone or preferably in combination with other methods of treatment as otherwise described herein.

In still another embodiment, the invention provides a method of treating a subject who suffers from, or who is at risk of developing cancer, especially breast or prostate cancer, the method comprising administering to the subject to a therapeutically effective amount of a lipid-lowering drug (e.g. a statin such as cerivastatin, fluvastatin, lovastatin, pitavastatin, pravastatin, rosuvastatin or simvastatin, most preferably simvastatin) which increases the level of irisin in the subject's serum or plasma.

In still another embodiment, the invention provides a method of treating a subject who suffers from, or who is at risk of developing cancer, especially breast or prostate cancer, the method comprising administering to the subject to a therapeutically effective amount of a nucleic acid encoding FNDC5. Preferably, the subject's muscles cells are transfected with a vector which contains a nucleic acid encoding FNDC5 and which upregulates muscle cell FNDC5 expression. Examples of such vectors include the human adenovirus Type 5 (dE1/E3) vector (CMV promoter) (Unigene ID Hs.524234), the pDONR223 and pDONR201 vectors and pENTR223 vector, among numerous others. Most of these vectors are commercially available or may be readily prepared using standard genetic engineering methods known in the art.

In still another embodiment, the invention provides a method of treating a subject who suffers from, or who is at risk of developing cancer, especially breast or prostate cancer, the method comprising administering to the subject to a therapeutically effective amount of metformin, alone or in combination with other agents which are described herein.

In still another embodiment, the invention provides a method of predicting the responsiveness to pharmaceutical therapy of a subject who suffers from a cancer, especially including breast or prostate cancer, the method comprising measuring irisin levels in a biological sample taken from the subject (e.g. circulating irisin levels in a sample of the subject's plasma or serum) and comparing measured irisin levels to a reference value, wherein increased circulating irisin levels correlate to an increased responsiveness to pharmaceutical therapy.

In still another embodiment, the invention provides a method of predicting the responsiveness to pharmaceutical therapy of a subject who suffers from cancer, in particular, breast or prostate cancer, among others, the method comprising measuring FNDC5 expression-associated irisin levels in a muscle cell sample taken from the subject and/or the subject's plasma or serum irisin levels, and comparing measured FNDC5 expression-associated irisin levels and/or plasma or serum irisin levels to a reference value, wherein increased FNDC5 expression-associated irisin levels, or increased plasma or serum irisin levels, correlate to an increased responsiveness to pharmaceutical therapy.

In still another embodiment, the invention provides a method of screening a composition to determine whether it is effective in the treatment of cancer, in particular breast or prostate cancer, the method comprising contacting a cell which expresses FNDC5 (preferably a human muscle cell) with the composition, measuring the cell's relative increase or decrease in FNDC5 expression-associated irisin levels, and correlating FNDC5 expression-associated irisin levels with an increased likelihood that the composition is effective in the treatment of breast cancer.

In still another embodiment, the invention provides a kit comprising (a) at least one cell type selected from the group consisting of human non-malignant breast epithelial cells (MCF-10a) malignant breast epithelial cells (MCF-7), non-malignant prostate cancer cells (RWPE-1), malignant prostate cancer cells (PC3 or LNCaP), (b) human recombinant non-modified irisin (INM) and/or human recombinant modified and active (glycosylated) irisin (IM), and (c) instructions correlating cell viability with treatment by irisin and one or more additional anti-cancer agents.

The aforementioned novel methods of treatment, pharmaceutical compositions and diagnostic and screening methods constitute a significant advance in treating cancer, especially breast and/or prostate cancer patients who have proven refractory to conventional therapeutic regimens especially including drug/multiple drug resistant cancers, recurrent cancers and/or metastatic cancers, and facilitate the early diagnosis and optimum treatment of patients before the onset and during the progression of cancer, especially breast and/or prostate cancer. The novel methods of treatment and pharmaceutical compositions conceivably can increase cancer, especially breast and or prostate cancer progression-free survival and time to cancer, especially breast and/or prostate cancer progression in metastatic breast cancer patients. The present invention will hopefully result in an objective, complete or partial response in such patients.

These and other aspects are described further in the Detailed Description of the Invention, which follows.

NOTES: * indicates $P<0.05$ and *** indicates $P<0.001$ compared with control. As determined in the experiment of Example 1.

Figure 3:
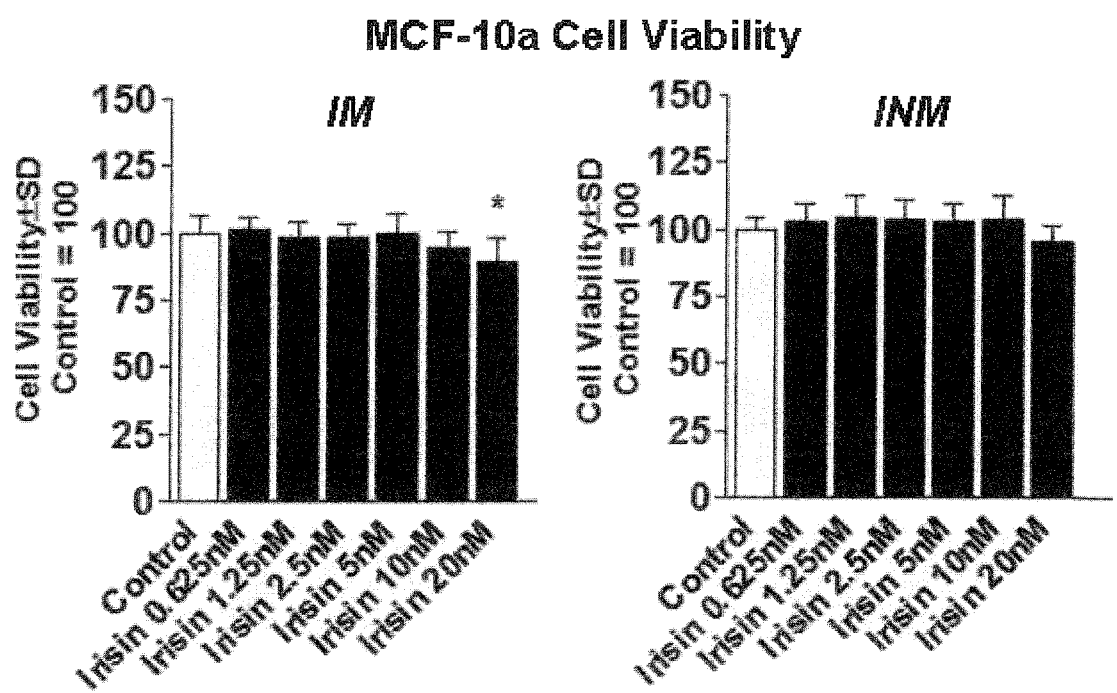
FIG. 3. (Supporting Information FIG. 1). MCF-10a Irisin Tolerance. Cell viability of MCF-10a cells following treatment with modified irisin (IM) and non-modified irisin (INM) with concentrations ranging from 0.625 nM to 20 nM. NOTES: * indicates $P<0.05$ and *** indicates $P<0.001$ compared with control. As determined in the experiment of Example 1.
Figure 4A:
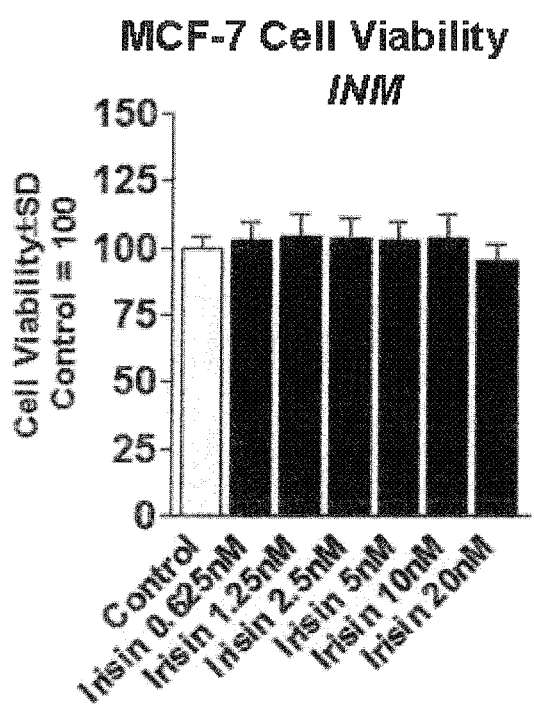
FIG. 4. (Supporting Information FIG. 2). This figure shows MCF-7 Irisin Tolerance and Doxorubicin Dynamics. (A) Cell viability of MCF-7 cells following treatment with concentrations of non-modified irisin (INM) ranging from 0.625 nM to 20 nM. (B) MCF-7 cells treated with INM at 2 nM with or without varied Dox (0.156 μM to 10 μM) for 24 hours.
Figure 4B:
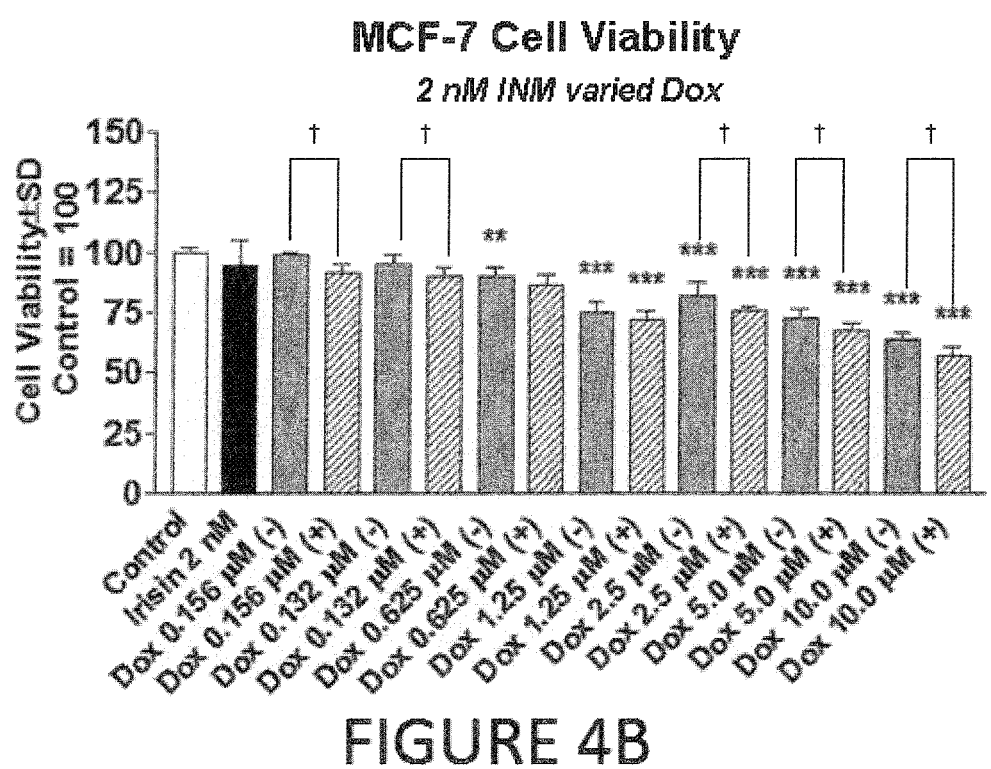
Figure 5:
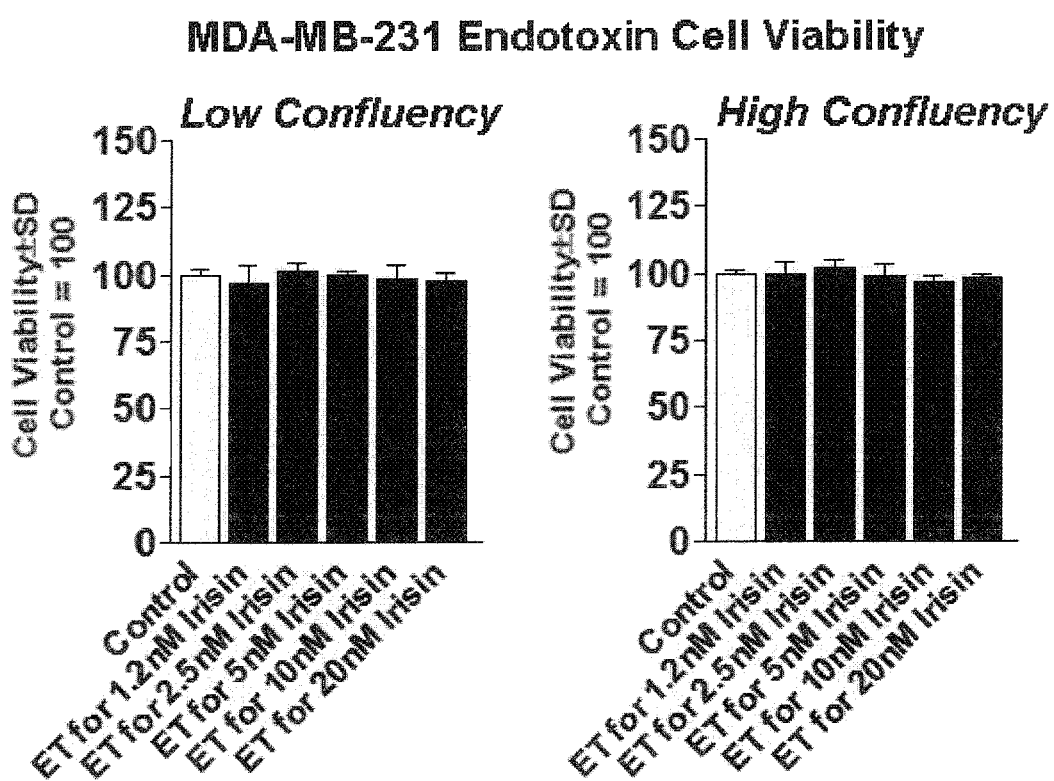

FIG. 5. (Supporting Information FIG. 3). This figure illustrates MDA-MB-231 endotoxin cell viability and different irisin levels, as determined in the experiment of Example 1.

Figure 6:
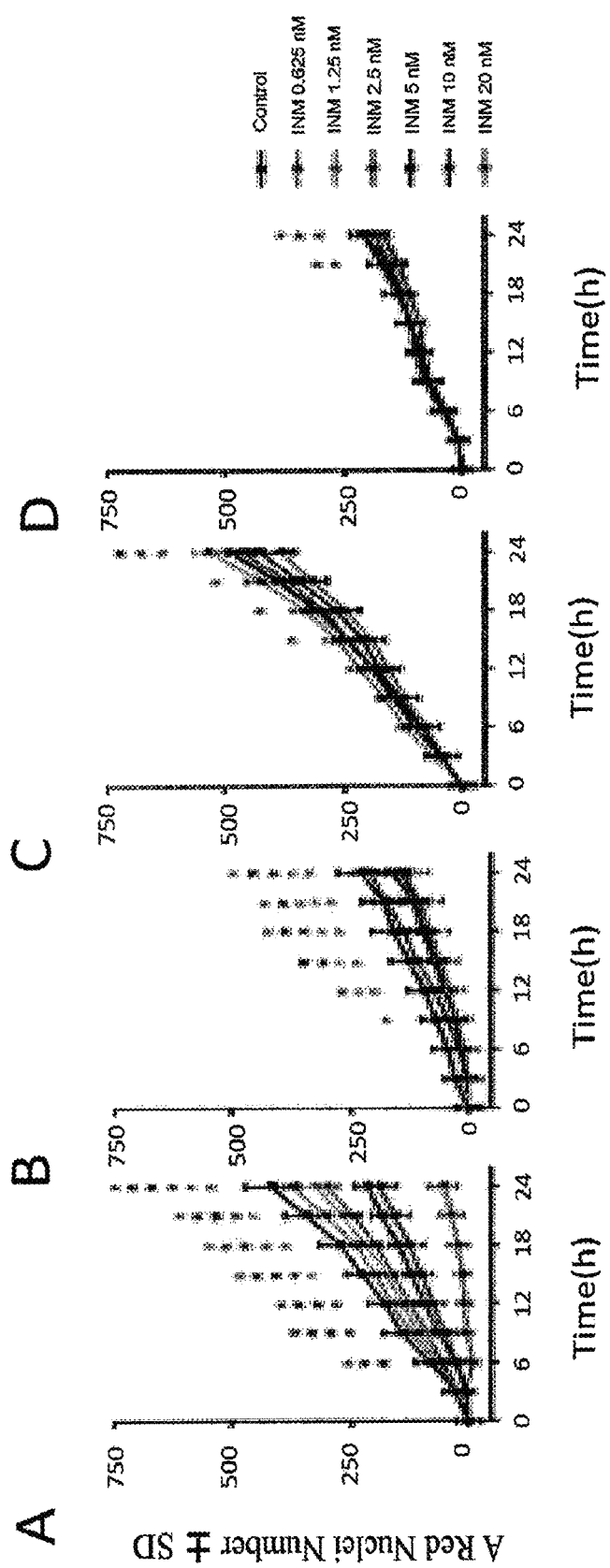

FIG. 6. FIG. 6 shows cell proliferation. (A) Cell proliferation of PC3 (B) LNCAP, (C) DU145, and (D) RWPE1 cells treated with control media, or various concentrations of non-modified irisin (INM) for 24 hours. NOTES: * indicates $P<0.05$ and *** indicates $P<0.001$ compared with control.

Figure 7:
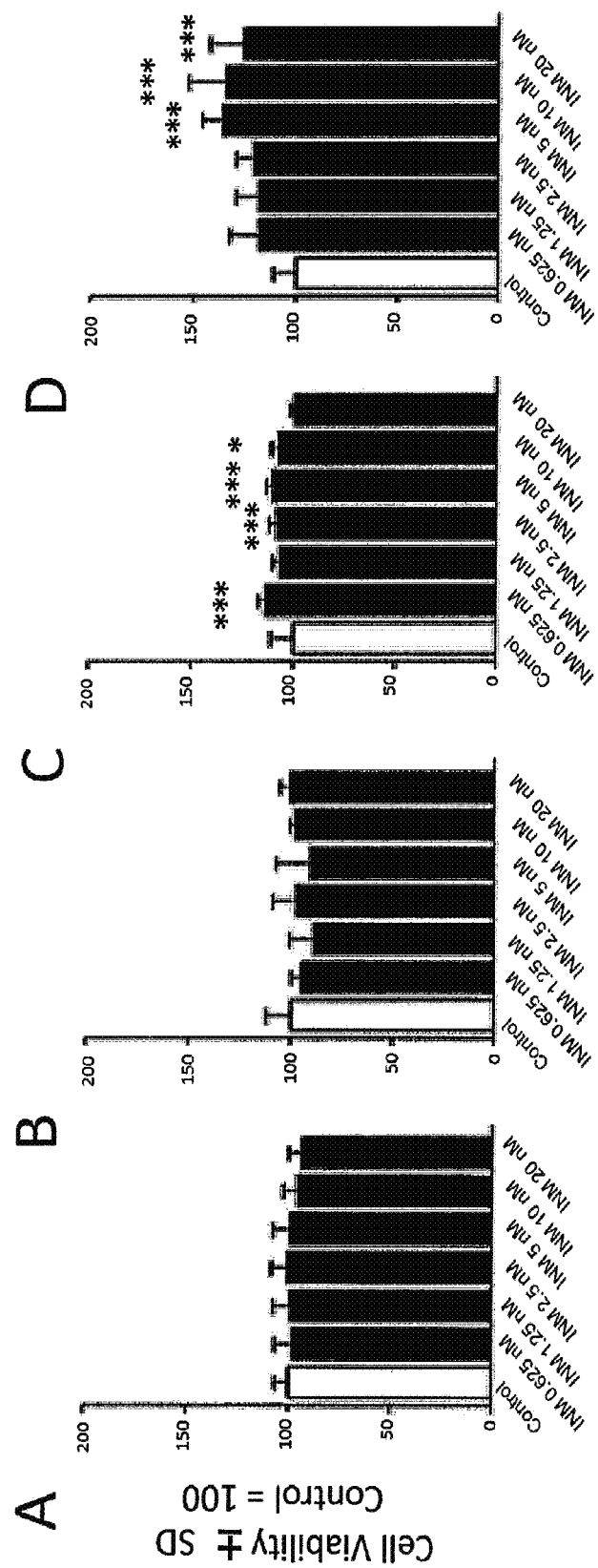

FIG. 7. shows cell viability. (A) Cell viability of PC3 (B) LNCaP, (C) DU145, and (D) RWPE1 cells treated with control media, or various concentrations of non-modified irisin (INM) for 24 hours. NOTES: * indicates $P<0.05$ and *** indicates $P<0.001$ compared with control.

DETAILED DESCRIPTION OF THE INVENTION

The following terms are used throughout the specification to describe the present invention. Where a term is not given a specific definition herein, that term is to be given the same meaning as understood by those of ordinary skill in the art. The definitions given to the disease states or conditions which may be treated using one or more of the compounds according to the present invention are those which are generally known in the art.

The singular forms "a," "an," and "the," include plural referents unless expressly and unequivocally limited to one referent. Thus, for example, reference to "an inhibitor" can include two or more different compounds. As used herein, the term "include" and its grammatical variants are intended to be non-limiting, such that recitation of items in a list is not to the exclusion of other like items that can be substituted or other items that can be added to the listed items.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Haines & Higgins eds., 1985, "Nucleic Acid Hybridization"; Haines & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, such as coding regions, and non-coding regions such as regulatory sequences (e.g., promoters or transcriptional terminators). A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

The term "patient" or "subject" is used throughout the specification to describe an animal; preferably a human, to whom treatment, including prophylactic treatment, with the compositions according to the present invention is provided. For treatment of those infections, conditions or disease states which are specific for a specific animal such as a human patient, the term patient refers to that specific animal.

Purely by way of example, a comparison of irisin plasma or serum levels or FNDC5 expression-associated irisin levels in a muscle cell levels to corresponding reference values, or a comparison of the expression levels of genes encoding FNDC5 to a reference expression pattern profile, can reflect cellular or expression level differences of about between about 5-10%, or about 10-15%, or about 15-20%, or about 20-25%, or about 25-30%, or about 30-35%, or about 35-40%, or about 40-45%, or about 45-50%, or about 50-55%, or about 55-60%, or about 60-65%, or about 65-70%, or about 70-75%, or about 75-80%, or about 80-85%, or about 85-90%, or about 90-95%, or about 95-100%, or about 100-110%, or about 110-120%, or about 120-130%, or about 130-140%, or about 140-150%, or about 150-160%, or about 160-170%, or about 170-180%, or about 180-190%, or 190-200%, or 200-210%, or 210-220%, or 220-230%, or 230-240%, or 240-250%, or 250-260%, or about 260-270%, or about 270-280%, or about 280-290%, or about 290-300%, or cellular or expression level differences of about between about ±50% to about ±0.5%, or about ±45% to about ±1%, or about ±40% to about ±1.5%, or about ±35% to about ±2.0%, or about ±30% to about ±2.5%, or about ±25% to about ±3.0%, or about ±20% to about ±3.5%, or about ±15% to about ±4.0%, or about ±10% to about ±5.0%, or about ±9% to about ±1.0%, or about ±8% to about ±2%, or about ±7% to about ±3%, or about ±6% to about ±5%, or about ±5%, or about ±4.5%, or about ±4.0%, or about ±3.5%, or about ±3.0%, or about ±2.5%, or about ±2.0%, or about ±1.5%, or about ±1.0%.

The terms "composition" as used herein to refer to any specific chemical compound, polypeptide, antibody or complex disclosed herein or otherwise known to those of ordinary skill in the art. When the term refers to a single small molecule it includes stereoisomers and/or optical isomers (including racemic mixtures) of that molecule, as well as active metabolites and/or pharmaceutically active salts thereof.

The term "irisin" is used to describe a number of polypeptide compounds which can be used to treat cancer in the present invention, including the preferred active compositions according to the present invention which includes both the polypeptide (SEQ ID NO: 1, below) and the polypeptide of identical sequence which is glycosylated at the 8 and 53 asparagine positions (glycosylated or irisin IM) as well as polypeptide variants which have at least about a 90% sequence identity, and preferably at least about 95% sequence identify (about 96%, about 97%, about 98% and about 99% sequence identify) to the polypeptide of SEQ ID NO: 1, above. Irisin is a hormonal messenger derived from fibronectin type III domain-containing protein 5 (FNDC5), a membrane-spanning protein of 196 aa. Aside from a short signal peptide, FNDC5 predominantly consists of an extracellular region containing the fibronectin type III (FnIII) domain, separated from a small cytoplasmic region by the helical transmembrane section. Irisin is a 112 aa peptide with an estimated molecular mass of 22 kDa which includes the 91 aa extracellular FnIII domain, cleaved from the carboxy terminus of FNDC5. Irisin represents amino acid residues 16-127 of FNDC5.

Non-modified irisin (INM) has the following preferred polypeptide sequence (SEQ ID NO: 1):
dspsapvnvt vrhlkansav vswdvledev vigfaisqqk kdvrmlrfiq evntttrsca lwdleedtey ivhvqaisiq gqspasepvl fktpreaekm asknkdevtm ke (SEQ ID NO: 1)
Modified irisin is glycosylated at either and preferably both asparagine 8 and asparagine 53 positions of SEQ ID NO: 1. A preferred non-modified Irisin variant (which has 99% sequence identity to the Irisin of SEQ ID NO: 1) is the polypeptide of SEQ ID NO: 2 below:
spsapvnvt vrhlkansav vswdvledev vigfaisqqk kdvrmlrfiq evntttrsca lwdleedtey ivhvqaisiq gqspasepvl fktpreaekm asknkdevtm ke (SEQ ID NO: 2)

Note that the first amino acid-aspartic acid has been removed from the sequence of SEQ ID NO:1 to provide the polypeptide of SEQ ID NO: 2).

A modified Irisin variant of SEQ ID NO: 2 is glycosylated at asparagine 7 and/or 52 positions, preferably both positions.

Irisin polypeptide which includes the linker sequence aegss at the amino end of the polypeptide and has about a 95% sequence identity to SEQ ID NO:1 above has the following sequence:

aegss dspsapvnvt vrhlkansav vswdvledev vigfaisqqk kdvrmlrfiq evntttrsca lwdleedtey ivhvqaisiq gqspasepvl fktpreaekm asknkdevtm ke (SEQ ID NO:3)

The above non-modified Irisin polypeptide which includes the linker sequence may be further modified with glycosyl groups at asparagine 8 and 53 amino acids.

Irisin as used in the present invention refers to both the non-modified irisin (INM) and the glycosylated irisin (IM), as well as various variants as described above and their corresponding pharmaceutically acceptable salts, with the INM of SEQ ID NO: 1 being preferred because of its heightened activity against cancer cells compared to the modified, glycosylated version of the same polypeptide and various Irisin variants described which also may be used in the present invention.

The terms "effective amount" or "pharmaceutically effective amount" are used throughout the specification to describe concentrations or amounts of compounds, compositions or other components which are used in amounts, within the context of their use, to produce an intended effect according to the present invention. The compound or component may be used to produce a favorable change in a disease or condition treated, whether that change is a remission, a favorable physiological result, a reversal or attenuation of a disease state or condition treated, the prevention or the reduction in the likelihood of a condition or disease-state occurring, depending upon the disease or condition treated. Where compounds are used in combination, each of the compounds is used in an effective amount, wherein an effective amount may include a synergistic amount. In many instances, the term "effective amount" refers to that amount which upregulates expression of FNDC5 or increases irisin levels in plasma or serum, or improves the status of a cancer, especially a breast or prostate cancer patient and consequently results in a diminution of resistance to a therapeutic approach, e.g. to symptoms or results in an improvement of symptoms associated with a cancer, in particular a breast or prostate cancer tumor which is non-responsive or intrinsically resistant to anti-estrogen therapy, a chemotherapy regimen (especially recurrent cancer) or an alternative therapy such as radiation therapy.

The amount of irisin used in the present invention may vary according to the nature of the inhibitor, the age and weight of the patient and numerous other factors which may influence the bioavailability and pharmacokinetics of the inhibitor. The amount of irisin which is administered to a patient generally ranges from about 0.001 mg/kg to about 50 mg/kg or more, about 0.5 mg/kg to about 25 mg/kg, about 0.1 to about 15 mg/kg, about 1 mg to about 10 mg/kg per day and otherwise described herein. The person of ordinary skill may easily recognize variations in dosage schedules or amounts to be made during the course of therapy.

The term "neoplasia" or "neoplasm" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and may invade surrounding tissues. As used herein, the term neoplasia/neoplasm is used to describe all pathological process associated with breast cancer and pancreatic cancer and their metastasis. The term "tumor" is a type of neoplasia used to describe a malignant or benign growth or tumefacent.

Neoplasia refers to the uncontrolled and progressive multiplication of tumor cells, under conditions that would not elicit, or would cause cessation of, multiplication of normal cells. Neoplasia results in a "neoplasm", which is defined herein to mean any new and abnormal growth, particularly a new growth of tissue, in which the growth of cells is uncontrolled and progressive. Thus, neoplasia includes "cancer", which herein refers to a proliferation of tumor cells having the unique trait of loss of normal controls, resulting in unregulated growth, lack of differentiation, local tissue invasion, and/or metastasis. The cancer may be "naïve", metastatic or recurrent and includes drug resistant and multiple drug resistant cancers, all of which may be treated using compounds according to the present invention.

As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of anaplasia, or loss of differentiation and orientation of cells, and have the properties of invasion and metastasis. Examples of neoplasms or neoplasias include, without limitation, carcinomas (e.g., squamous-cell carcinomas, adenocarcinomas, hepatocellular carcinomas, and renal cell carcinomas), particularly those of the bladder, bowel, breast, cervix, endometrical, colon, esophagus, head, kidney, liver, lung (including large cell and small cell lung cancer), head, neck, throat, larynx, ovary, pancreas, prostate, stomach and thyroid; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcoma, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine/endometrial cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas, which may be treated by one or more compounds according to the present invention. See, (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991. In preferred aspects of the invention, the method of treatment preferably includes the treatment of a solid tumor. In other preferred aspects, the present invention is directed to the treatment of cancers which are drug resistant (including multiple drug resistant cancers), recurrent (recurrent cancers are often chemotherapy resistant) and metastatic cancers.

The term "prophylactic" is used to describe the use of a compound described herein which reduces the likelihood of an occurrence of a condition or disease state in a patient or subject. The term "reducing the likelihood" refers to the fact that in a given population of patients, the present invention may be used to reduce the likelihood of an occurrence, recurrence or metastasis of disease in one or more patients within that population of all patients, rather than prevent, in all patients, the occurrence, recurrence or metastasis of a disease state.

The term "pharmaceutically acceptable" refers to a salt form or other derivative (such as an active metabolite or prodrug form) of a composition which upregulates expression of FNDC5 or increases irisin plasma or serum levels, or a carrier, additive or excipient which is not unacceptably toxic to the subject to which it is administered. This term may also refer to a salt form of irisin (INM or IM).

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states associated with breast cancer and pancreatic cancer and embraces or encompasses the pathological process associated with malignant hematogenous, ascetic and solid tumors. Numerous cancers are described hereinabove.

The terms "additional anticancer agent" and "chemotherapeutic agent" include, but are not limited to, compositions selected from the group consisting of microtubule-stabilizing agents, microtubule-disruptor agents, alkylating agents, antimetabolites, epidophyllotoxins, antineoplastic enzymes, topoisomerase inhibitors, inhibitors of cell cycle progression, and platinum coordination complexes, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody or a mixture thereof. These also may be selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others.

"Breast cancer" includes ductal carcinoma in situ (DCIS) and invasive breast cancer. Breast cancers can occur in milk ducts, milk-producing lobules and connective tissues. "Breast cancer" as defined herein includes estrogen receptor (ER) negative and hormone receptor (HR) negative, and also can be categorized as Group 3 (HER-2 positive) or Group 4 (basal-like).

The term "prostate cancer" is used to describe a disease in which cancer develops in the prostate, a gland in the male reproductive system. It occurs when cells of the prostate mutate and begin to multiply uncontrollably. These cells may metastasize (metastatic prostate cancer) from the prostate to virtually any other part of the body, particularly the bones and lymph nodes, but the kidney, bladder and even the brain, among other tissues. Prostate cancer may cause pain, difficulty in urinating, problems during sexual intercourse, erectile dysfunction. Other symptoms can potentially develop during later stages of the disease.

Rates of detection of prostate cancers vary widely across the world, with South and East Asia detecting less frequently than in Europe, and especially the United States. Prostate cancer develops most frequently in men over the age of fifty and is one of the most prevalent types of cancer in men. However, many men who develop prostate cancer never have symptoms, undergo no therapy, and eventually die of other causes. This is because cancer of the prostate is, in most cases, slow-growing, and because most of those affected are over the age of 60. Hence, they often die of causes unrelated to the prostate cancer. Many factors, including genetics and diet, have been implicated in the development of prostate cancer. The presence of prostate cancer may be indicated by symptoms, physical examination, prostate specific antigen (PSA), or biopsy. There is concern about the accuracy of the PSA test and its usefulness in screening. Suspected prostate cancer is typically confirmed by taking a biopsy of the prostate and examining it under a microscope. Further tests, such as CT scans and bone scans, may be performed to determine whether prostate cancer has spread.

Treatment options for prostate cancer with intent to cure are primarily surgery and radiation therapy. Other treatments such as hormonal therapy, chemotherapy, proton therapy, cryosurgery, high intensity focused ultrasound (HIFU) also exist depending on the clinical scenario and desired outcome.

The age and underlying health of the man, the extent of metastasis, appearance under the microscope, and response of the cancer to initial treatment are important in determining the outcome of the disease. The decision whether or not to treat localized prostate cancer (a tumor that is contained within the prostate) with curative intent is a patient trade-off between the expected beneficial and harmful effects in terms of patient survival and quality of life.

An important part of evaluating prostate cancer is determining the stage, or how far the cancer has spread. Knowing the stage helps define prognosis and is useful when selecting therapies. The most common system is the four-stage TNS system (abbreviated from Tumor/Nodes/Metastases). Its components include the size of the tumor, the number of involved lymph nodes, and the presence of any other metasteses.

The most important distinction made by any staging system is whether or not the cancer is still confined to the prostate or is metastatic. In the TNM system, clinical T1 and T2 cancers are found only in the prostate, while T3 and T4 cancers have spread elsewhere and metastasized into other tissue. Several tests can be used to look for evidence of spread. These include computeed tomography to evaluate spread within the pelvis, bone scans to look for spread to the bones, and endorectal coil magnetic resonance imaging to closely evaluate the prostatic capsule and the smnial vesicles. Bone scans often reveal osteoblastic appearance due to increased bone density in the areas of bone metastasis—opposite to what is found in many other cancers that metastasize. Computeed tomography (CT) and magnetic resonance imaging (MRI) currently do not add any significant information in the assessment of possible lymph node metastases in patients with prostate cancer according to a meta-analysis.

Prostate cancer is relatively easy to treat if found early. After a prostate biopsy, a pathologist looks at the samples under a microscope. If cancer is present, the pathologist reports the grade of the tumor. The grade tells how much the tumor tissue differs from normal prostate tissue and suggests how fast the tumor is likely to grow. The Gleason system is used to grade prostate tumors from 2 to 10, where a Gleason score of 10 indicates the most abnormalities. The pathologist assigns a number from 1 to 5 for the most common pattern observed under the microscope, then does the same for the second most common pattern. The sum of these two numbers is the Gleason score. The Whitmore-Jewitt stage is another method sometimes used. Proper grading of the tumor is critical, since the grade of the tumor is one of the major factors used to determine the treatment recommendation.

Early prostate cancer usually causes no symptoms. Often it is diagnosed during the workup for an elevated PSA noticed during a routine checkup. Sometimes, however, prostate cancer does cause symptoms, often similar to those of diseases such as benign prostatic hypertrophy. These include frequent urination, increased urination at night, difficulty starting and maintaining a steady stream of urine, blood in the urine, and painful urination. Prostate cancer is associated with urinary dysfunction as the prostate gland surrounds the prostatic urethra. Changes within the gland therefore directly affect urinary function. Because the vas deferens deposits seminal fluid into the prostatic urethra, and secretions from the prostate gland itself are included in semen content, prostate cancer may also cause problems with sexual function and performance, such as difficulty achieving erection or painful ejaculation.

Advanced prostate cancer can spread to other parts of the body and this may cause additional symptoms. The most common symptom is bone pain, often in the vertebrae, pelvis or ribs. Spread of cancer into other bones such as the femur is usually to the proximal part of the bone. Prostate cancer in the spinespine can also compress the spinal cord, causing leg weakness and urinary and fecal incontinence.

The specific causes of prostate cancer remain unknown. A man's risk of developing prostate cancer is related to his age, genetics, race, diet, lifestyle, medications, and other factors. The primary risk factor is age. Prostate cancer is uncommon in men less than 45, but becomes more common with advancing age. The average age at the time of diagnosis is 70. However, many men never know they have prostate cancer.

A man's genetic background contributes to his risk of developing prostate cancer. This is suggested by an increased incidence of prostate cancer found in certain racial groups, in identical twins of men with prostate cancer, and in men with certain genes. Men who have a brother or father with prostate cancer have twice the usual risk of developing prostate cancer. Studies of twins in Scandinavia suggest that forty percent of prostate cancer risk can be explained by inherited factors. However, no single gene is responsible for prostate cancer; many different genes have been implicated. Two genes (BRCA1 and BRCA2) that are important risk factors for ovarian cancer and breast cancer in women have also been implicated in prostate cancer.

Dietary amounts of certain foods, vitamins and minerals can contribute to prostate cancer risk. Dietary factors that may increase prostate cancer risk include low intake of vitamin E, the mineral selenium, green tea and vitamin D. A large study has implicated dairy, specifically low-fat milk and other dairy products to which vitamin A palmitate has been added. This form of synthetic vitamin A has been linked to prostate cancer because it reacts with zinc and protein to form an unabsorbable complex. Prostate cancer has also been linked to the inclusion of bovine somatotropin hormone in certain dairy products.

There are also some links between prostate cancer and medications, medical procedures, and medical conditions. Daily use of anti-inflammatory medicines such as aspiring, ibuprofen or naproxen may decrease prostate cancer risk. Use of the cholesterole-lowering drugs known as the statins may also decrease prostate cancer risk. Infection or inflammation of the prostate (prostatitis) may increase the chance for prostate cancer, and infection with the sexually transmitted infections, chlamydia, gonorrhea, or syphilis seems to increase risk. Obesity and elevated blood levels of testosterone may increase the risk for prostate cancer.

Prostate cancer is classified as an adenocarcinoma, or glandular cancer, that begins when normal semen-secreting prostate gland cells mutate into cancer cells. The region of prostate gland where the adenocarcinoma is most common is the peripheral zone. Initially, small clumps of cancer cells remain confined to otherwise normal prostate glands, a condition known as carcinoma in situ or prostatic intraepithelial neoplasia (PIN). Although there is no proof that PIN is a cancer precursor, it is closely associated with cancer. Over time these cancer cells begin to multiply and spread to the surrounding prostate tissue (the stroma) forming a tumor. Eventually, the tumor may grow large enough to invade nearby organs such as the seminal vesicles or the rectum, or the tumor cells may develop the ability to travel in the bloodstream and lymphatic system. Prostate cancer is considered a malignant tumor because it is a mass of cells which can invade other parts of the body. This invasion of other organs is called metastasis. Prostate cancer most commonly metastasizes to the bones, lymph nodes, rectum, and bladder.

In prostate cancer, the regular glands of the normal prostate are replaced by irregular glands and clumps of cells. When a man has symptoms of prostate cancer, or a screening test indicates an increased risk for cancer, more invasive evaluation is offered. The only test which can fully confirm the diagnosis of prostate cancer is a biopsy, the removal of small pieces of the prostate for microscopic examination. However, prior to a biopsy, several other tools may be used to gather more information about the prostate and the urinary tract. Cystoscopy shows the urinary tract from inside the bladder, using a thin, flexible camera tube inserted down the urethra. Transrectal ultrasonography creates a picture of the prostate using sound waves from a probe in the rectum.

After biopsy, the tissue samples are then examined under a microscope to determine whether cancer cells are present, and to evaluate the microscopic features (or Gleason score) of any cancer found. In addition, tissue samples may be stained for the presence of PSA and other tumor markers in order to determine the origin of malignant cells that have metastasized. A number of other potential approaches for diagnosis of prostate cancer are ongoing such as early prostate cancer antigen-2 (EPCA-2), and prostasome analysis.

In addition to therapy using the compounds according to the present invention, therapy (including prophylactic therapy) for prostate cancer supports roles in reducing prostate cancer for dietary selenium, vitamin E, lycopene, soy foods, vitamin D, green tea, omega-3 fatty acids and phytoestrogens. The selective estrogen receptor modulator drug toremifene has shown promise in early trials. Two medications which block the conversion of testosterone to dihydrotestosterone (and reduce the tendency toward cell growth), finasterid and dutasteride, are shown to be useful. The phytochemicals indole-3-carbinol and diindolylmethane, found in cruciferous vegetables (califlower and broccoli), have favorable antiandrogenic and immune modulating properties. Prostate cancer risk is decreased in a vegetarian diet.

Treatment for prostate cancer may involve active surveillance, surgery (prostatecomy or orchiectomy), radiation therapy including brachytherapy (prostate brachytherapy) and external beam radiation as well as hormonal therapy. There are several forms of hormonal therapy which include the following, each of which may be combined with compounds according to the present invention.

Antiandrogens such as flutamide, bicalutamide, nilutamide, and cyproterone acetate which directly block the actions of testosterone and DHT within prostate cancer cells.

Medications such as ketoconazole and aminoglutethimide which block the production of adrenal androgens such as DHEA. These medications are generally used only in combination with other methods that can block the 95% of androgens made by the testicles. These combined methods are called total androgen blockade (TAB), which can also be achieved using antiandrogens.

GnRH modulators, including agonists and antagonists. GnRH antagonists suppress the production of LH directly, while GnRH agonists suppress LH through the process of downregulation after an initial stimulation effect. Abarelix is an example of a GnRH antagonist, while the GnRH agonists include leuprolide, goserelin, triptorelin, and buserelin.

The use of abiraterone acetate can be used to reduce PSA levels and tumor sizes in aggressive end-stage prostate cancer for as high as 70% of patients. Sorafenib may also be used to treat metastatic prostate cancer.

Each treatment described above has disadvantages which limit its use in certain circumstances. GnRH agonists eventually cause the same side effects as orchiectomy but may cause worse symptoms at the beginning of treatment. When GnRH agonists are first used, testosterone surges can lead to increased bone pain from metastatic cancer, so antiandrogens or abarelix are often added to blunt these side effects. Estrogens are not commonly used because they increase the risk for cardiovascular disease and blood clots. The antiandrogens do not generally cause impotence and usually cause less loss of bone and muscle mass. Ketoconazole can cause liver damage with prolonged use, and aminoglutethimide can cause skin rashes.

Palliative care for advanced stage prostate cancer focuses on extending life and relieving the symptoms of metastatic disease. As noted above, abiraterone acetate shows some promise in treating advance stage prostate cancer as does sorafenib. Chemotherapy may be offered to slow disease progression and postpone symptoms. The most commonly used regimen combines the chemotherapeutic drug docetaxel with a corticosteroid such as prednisone. Bisphosphonates such as zoledronic acid have been shown to delay skeletal complications such as fractures or the need for radiation therapy in patients with hormone-refractory metastatic prostate cancer. Alpharadin may be used to target bone metastasis. The phase II testing shows prolonged patient survival times, reduced pain and improved quality of life.

Bone pain due to metastatic disease is treated with opioid pain relievers such as morphine and oxycodone. External beam radiation therapy directed at bone metastases may provide pain relief. Injections of certain radioisotopes, such as strontium-89, phosphorous-32, or samarium-153, also target bone metastases and may help relieve pain.

As an alternative to active surveillance or definitive treatments, alternative therapies may also be used for the management of prostate cancer. PSA has been shown to be lowered in men with apparent localized prostate cancer using a vegan diet (fish allowed), regular exercise, and stress reduction. Many other single agents have been shown to reduce PSA, slow PSA doubling times, or have similar effects on secondary markers in men with localized cancer in short term trials, such as pomegranate juice or genistein, an isoflavone found in various legumes.

Manifestations or secondary conditions or effects of metastatic and advanced prostate cancer may include anemia, bone marrow suppression, weight loss, pathologic fractures, spinal cord compression, pain, hematuria, ureteral and/or bladder outlet obstruction, urinary retention, chronic renal failure, urinary incontinence, and symptoms related to bony or soft-tissue metastases, among others.

Additional prostate drugs which can be used in combination with the irisin and related compounds according to the present invention include, for example, the enlarged prostate drugs/agents, as well as eulexin, flutamide, goserelin, leuprolide, lupron, nilandron, nilutamide, zoladex and mixtures thereof. Enlarged prostate drugs/agents as above, include for example, ambenyl, ambophen, amgenal, atrosept, bromanyl, bromodiphenhydramine-codeine, bromotuss-codeine, cardura, chlorpheniramine-hydrocodone, ciclopirox, clotrimazole-betamethasone, dolsed, dutasteride, finasteride, flomax, gecil, hexalol, lamisil, lanased, loprox, lotrisone, methenamine, methen-bella-meth Bl-phen sal, meth-hyos-atrp-M blue-BA-phsal, MHP-A, mybanil, prosed/DS, Ro-Sed, S-T Forte, tamsulosin, terbinafine, trac, tussionex, ty-methate, uramine, uratin, uretron, uridon, uroves, urstat, usept and mixtures thereof.

The terms "HER2 positive metastatic breast cancer", "growth inhibitory HER2 antibody (e.g. pertuzumab or trastuzumab), "HER2 dimerization inhibitor antibody" are defined and used in the same manner as in U.S. Patent Application Document No. 20140044704.

"Human epidermal growth factor receptor-2 (HER-2) positive breast cancer represents a special subtype that has clear epidemiological, clinical, molecular and prognostic differences that make it a separate entity with recognized worse prognosis and poor response to conventional chemotherapy agents alone. The epidermal growth factor receptor (EGFR) family is composed by four different receptors: EGFR (ErbB1/HER-1), ErbB2 (HER-2/Neu), ErbB3 (HER-3) and ERbB4 (HER-4). These membrane receptors have an intracellular domain with tyrosine kinase activity." Gonzalo, et al., "Therapeutic options for HER-2 positive breast cancer: Perspectives and future directions", *World J Clin Oncol.* 2014 Aug. 10; 5(3): 440-454.

"In breast cancer cells, HER-2 and EGFR are frequently over-expressed, conferring an aggressive tumor behavior and consequently, increased mortality in this population. HER-2 can be amplified in 20%-25% of breast cancers and is associated with adverse prognostic outcomes in early and advanced disease. Trastuzumab (Herceptin®) is a monoclonal antibody approved for breast cancer treatment directed against HER-2. It binds to HER-2 in its extracellular domain. Pertuzumab (Perjeta®) is a humanized recombinant monoclonal antibody that binds HER-2 at a different extracellular domain than trastuzumab. Trastuzumab blocks homo-dimerization but cannot inhibit hetero-dimerization. Pertuzumab prevents also hetero-dimerization, resulting in more potent growth inhibition. Ado-trastuzumab emtansine (Kadcyla®) is a conjugation of trastuzumab with a potent microtubule inhibitor agent, derivative of maytansine (DM-1). This molecule has 3 properties, anti-HER-2 inhibition by trastuzumab, cytotoxic effect by DM-1 and certain level of tissue specificity by directing the cytotoxic agent only to those cells that express HER-2. It has recently being approved for refractory metastatic disease. Lapatinib (Tykerb®) is the only intracellular blocker approved. It is a dual reversible tyrosine kinase inhibitor of HER-2 and EGFR. It acts on both receptors simultaneously, achieving greater inhibitory effects. In the adjuvant scenario, treatment with trastuzumab is the standard of care for patients with HER-2 over-expressing breast cancer. Trastuzumab can be administered in combination with paclitaxel or docetaxel following an anthracycline-based chemotherapy (i.e., doxorubicin and cyclophosphamide) or be given concurrently with carboplatin and docetaxel." Id.

"Increased breast cancer progression-free survival" and "time to breast cancer progression" are defined in U.S. Patent Application Document No. 20140044704 and those terms are used in the same manner herein.

"Alternative cancer therapies" refer to cancer therapies including, for example, androgen deprivation (for prostate cancer), radiation therapy, hormonal therapy, proton therapy, cryosurgery, high intensity focused ultrasound (HIFU) and heat and cold therapy. These various additional approaches can be used in conjunction with the present invention in order to facilitate treatment of a subject or patient with cancer.

The term "coadministration" or "combination therapy" is used to describe a therapy in which at least two active compounds/compositions in effective amounts are used to treat cancer as described herein at the same time. Although the term coadministration preferably includes the administration of two active compounds to the patient at the same time, it is not necessary that the compounds be administered to the patient at the same time or even serially (i.e. one right after the other), although effective amounts of the individual compounds will be present in the patient at the same time.

Pharmaceutical formulations according to the present invention include those suitable for oral, rectal, nasal, topical (including buccal and sub-lingual), vaginal or parenteral (including intramuscular, intrathecal, sub-cutaneous and intravenous) administration. Oral compositions or parenteral compositions may be preferred.

Formulations containing the compounds according to the present invention may take the form of liquid, solid, semi-solid or lyophilized powder forms, such as, for example, solutions, suspensions, emulsions, sustained-release formulations, tablets, capsules, powders, suppositories, creams, ointments, lotions, aerosols, patches or the like, preferably in unit dosage forms suitable for simple administration of precise dosages.

Pharmaceutical compositions according to the present invention typically include a conventional pharmaceutical carrier or excipient and may additionally include other medicinal agents, carriers, adjuvants, additives and the like. The weight percentage ratio of the one or more active ingredients to the one or more excipients can be between about 20:1 to about 1:60, or between about 15:1 to about 1:45, or between about 10:1 to about 1:40, or between about 9:1, 8:1, 7:1, 6:1, 5:1, 4:1, 3:1, 2:1 or 1:1 to about 1:2, 1:3, 1:4, 1:5, 1:6, 1:7, 1:8, 1:9, 1:10, 1:15, 1:20, 1:25, 1:30, or 1:35, and preferably is about 20:1, 19:1, 18:1, 17:1, 16:1, 15:1, 14:1, 13:1, 12:1, 11:1, 10:1, 9:1, 8:1, 7:1, 6:1 or 5:1. In some embodiments, formulations of the invention comprise between about 250 mg to about 500 mg, or between about 300 mg to about 450 mg, or about 325 mg to about 425 mg of total active ingredients and may optionally contain one or more suitable pharmaceutical excipients.

An injectable composition for parenteral administration (e.g. intravenous, intramuscular or intrathecal) will typically contain the compound in a suitable i.v. solution, such as sterile physiological salt solution. The composition may also be formulated as a suspension in an aqueous emulsion.

The invention of the present application anticipates administration of all dosage forms for the administration of compounds and/or compositions to be used to treat cancer.

Liquid compositions can be prepared by dissolving or dispersing the pharmaceutical composition comprising irisin or a composition which increases the level of irisin in the subject's serum or plasma, and optional pharmaceutical adjuvants, in a carrier, such as, for example, aqueous saline, aqueous dextrose, glycerol, or ethanol, to form a solution or suspension. For use in an oral liquid preparation, the composition may be prepared as a solution, suspension, emulsion, or syrup, being supplied either in liquid form or a dried form suitable for hydration in water or normal saline.

For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

Methods for preparing such dosage forms are known or are apparent to those skilled in the art; for example, see Remington's Pharmaceutical Sciences (17th Ed., Mack Pub. Co. 1985). The composition to be administered will contain a quantity of the selected compound in a pharmaceutically effective amount for therapeutic use in a biological system, including a patient or subject according to the present invention.

Methods of treating patients or subjects in need for a particular disease state or infection comprise administration of an effective amount of a pharmaceutical composition comprising therapeutic amounts of irisin and/or a composition which increases the level of irisin in a subject's serum or plasma and optionally at least one additional bioactive (e.g. anti-cancer) agent according to the present invention. The amount of active ingredient(s) used in the methods of treatment of the instant invention that may be combined with the carrier materials to produce a single dosage form will vary depending upon the host treated, the particular mode of administration. For example, the compositions could be formulated so that a therapeutically effective dosage of between about 0.01, 0.1, 1, 5, 10, 15, 20, 25, 30, 35, 40, 45, 50, 55, 60, 65, 70, 75, 80, 85, 90 or 100 mg/kg of patient/day or in some embodiments, greater than 100, 110, 120, 130, 140, 150, 160, 170, 180, 190 or 200 mg/kg of the novel compounds can be administered to a patient receiving these compositions.

Preferably, pharmaceutical compositions in dosage form according to the present invention comprise a therapeutically effective amount of at least 25 mg of irisin and/or a composition which increases the level of irisin in a subject's serum or plasma, at least 50 mg of irisin and/or a composition which increases the level of irisin in a subject's serum or plasma, at least 60 mg of irisin and/or a composition which increases the level of irisin in a subject's serum or plasma, at least 75 mg of irisin and/or a composition which increases the level of irisin in a subject's serum or plasma, at least 100 mg of irisin and/or a composition which increases the level of irisin in a subject's serum or plasma, at least 150 mg of irisin and/or a composition which increases the level of irisin in a subject's serum or plasma, at least 200 mg of irisin and/or a composition which increases the level of irisin in a subject's serum or plasma, at least 250 mg of irisin and/or a composition which increases the level of irisin in a subject's serum or plasma, at least 300 mg of irisin and/or a composition which increases the level of irisin in a subject's serum or plasma, about 350 mg of irisin and/or a composition which increases the level of irisin in a subject's serum or plasma, about 400 mg of irisin and/or a composition which increases the level of irisin in a subject's serum or plasma, about 500 mg of irisin and/or a composition which increases the level of irisin in a subject's serum or plasma, about 750 mg of irisin and/or a composition which increases the level of irisin in a subject's serum or plasma, about 1 g (1,000 mg) of irisin and/or a composition which increases the level of irisin in a subject's serum or plasma, alone or in combination with a therapeutically effective amount of at least one additional anti-cancer agent.

Preferred embodiments of the pharmaceutical compositions of the invention comprise between about 250 mg to about 500 mg, or between about 300 mg to about 450 mg, or about 325 mg to about 425 mg, most preferably about 380 mg of irisin and/or a composition which increases the level of irisin in a subject's serum or plasma.

These and other aspects of the invention are illustrated further in the following examples.

EXAMPLE 1

Effect of Irisin on Breast Cancer

Materials and Methods
Abbreviations Used:
IL-6—interleukin 6
TNF-α—tumor necrosis factor alpha
IM—modified irisin
INM—non-modified irisin
RFP—red fluorescent protein
Dox—Doxorubicin
Cell Culture and Treatments Human non-malignant breast epithelial cells (MCF-10a), malignant breast epithelial cells (MCF-7), and malignant aggressive breast epithelial cells (MDA-MB-231) were purchased from American Type Culture Collection (Manassas, Va.). Cells were maintained under standard conditions (37° C. in a 5% $CO_2$) using growth media as described in Supporting Information Table 1. Cells were treated with either human recombinant non-modified irisin (INM) from Cayman Chemical (Ann Arbor, Mich.) or human recombinant modified and active (glycosylated) irisin (IM) from PlexBio (San Francisco, Calif.) at concentrations ranging from 0.625 nM to 20 nM dissolved in culture media for 24 hours. Concentrations of irisin were determined empirically through pilot experiments based on and previously published observations.[9] MDA-MB-231 cells were labeled with red fluorescent protein (RFP) by lentiviral-transfection using CytoLight Red vector from Essen Bioscience (Ann. Arbor, Mich.). Successfully transfected cells were selected using media containing 1 µg/ml Puromycin and maintained in media containing 0.5 µg/ml Puromycin.

Cell Proliferation and Migration

RFP MDA-MB-231 cells were seeded overnight in 96-well plates at a density of 5,000 cells/well and treated with or without irisin at 2 nM (IM or INM) (N=64). Cell proliferation was measured by automated red object counting optimized for MDA-MB-231 cells using the Incucyte ZOOM live content imaging from Essen Bioscience (Ann Arbor, Mich.), measured every hour for 24 hours. Cell migration was assessed by applying a scratch through confluent cells cultured in a 96-well plate. Confluent cells were treated with or without irisin at 2 nM (IM or INM) for 24 hours prior to scratch. The cells were then rinsed and the media replaced with corresponding treatments. Migration was indicated by change in well confluence normalized to cell number (N=64).

Cell Viability

Cells were seeded overnight at a density of 5,000 cells/well, treated with or without varying concentrations of IM or INM (from 0.625 nM to 20 nM) (N=12). Cells were then incubated for 1 hour in medium containing 10% WST-1 cell proliferation reagent from Roche (Indianapolis, Ind.) and fluorescence was measured using a Wallac Victor3V 1420 Multilabel Counter from PerkinElmer (Waltham, Mass.). These methods were repeated with varying concentrations (from 0.156 µM to 10 µM) of the antineoplastic Doxorubicin (Dox) from Sigma (St. Louis, Mo.) dissolved in DMSO (using 0.1% for all treatments including control) with 2 nM IM or INM for 24 hours (N=8). At 24 hours, Dox uptake was measured using phase-contrast and fluorescence (N=24). Treatment concentrations and duration were determined empirically through pilot experiments and from previously published observations for Dox.[20]

NFκB-GFP Reporter System

Cells were transfected with a NFκB GFP-linked reporter system from Qiagen (Valencia, Calif.) before treatment with IM, INM, or TNF-α from R and D Systems (Minneapolis, Minn.) at various concentrations for 24 hours (N=12). NFκB activity was indicated by mean fluorescence measured by the Incucyte ZOOM as described above.

Caspase-3/7 Activity

Cells were co-treated as previously described (N=12) with a kinetic caspase-3/7 apoptosis reagent from Essen Bioscience (Ann Arbor, Mich.). Caspase-3/7 activity was indicated by mean green fluorescence measured by the Incucyte ZOOM as described above.

Statistical Analyses

Data was analyzed unsing ANOVA with Dunnett's post hoc pairwise comparisons. All data is represented as average±standard deviation with values of $p<0.05$ indicating statistical significance.

Results

Cell Proliferation and Migration

Figure 1A:
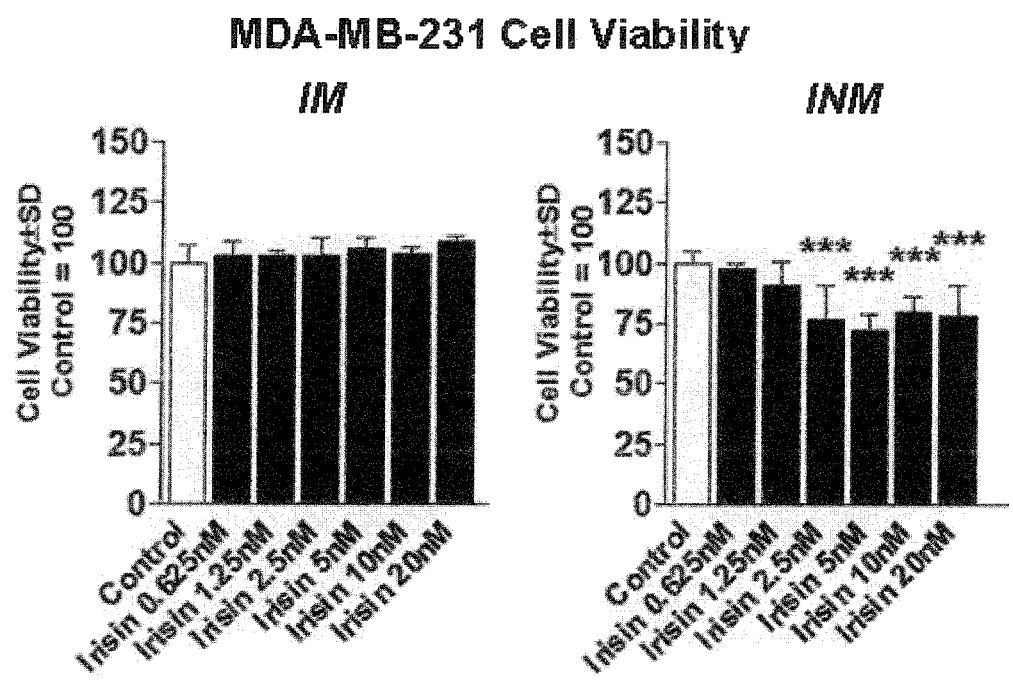
FIG. 1. Irisin Tolerance. (A) Cell viability of MDA-MB-231 cells treated with either control media, or concentrations of modified irisin (IM) or non-modified irisin (INM) ranging from 0.625 nM to 20 nM. (B) Cell proliferation of MDA-MB-231 cells following treatment with IM or INM at 2 nM as a change in red cell count (cell number) for 24 hours. (C) Cell migration of MDA-MB-231 cells following scratch and treatment with and without IM or INM at 2 nM for 24 hours (respective images shown at right). (D) Caspase-3/7 activity of MDA-MB-231 cells treated with IM, INM, or TNF-α for 24 hours. (E) NFκB activity of MDA-MB-231 cells treated with IM, INM, or TNF-α for 24 hours (respective images shown at right). NOTES: White size bar equals 200 μm. * indicates $P<0.05$ and *** indicates $P<0.001$ compared with control. † indicates $P<0.05$ compared with corresponding IM treatment group. As determined in the experiment of Example 1. (F) MDA-MB-231 cells treated with control media, 2 nM nonmodicfied irisin (INM), and 10 ng/TNF.
Figure 1B:
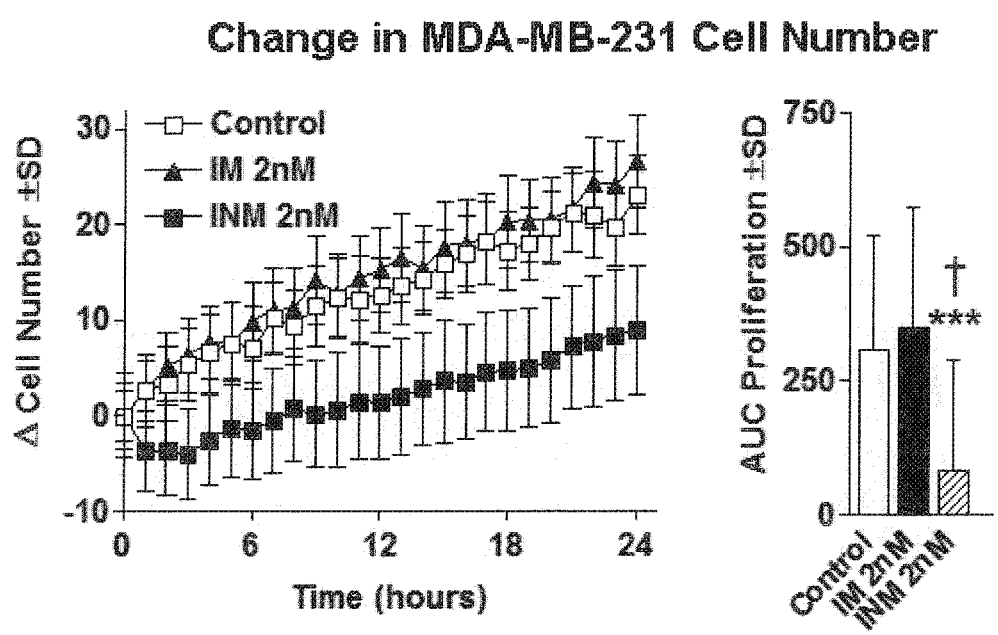
Figure 1C:
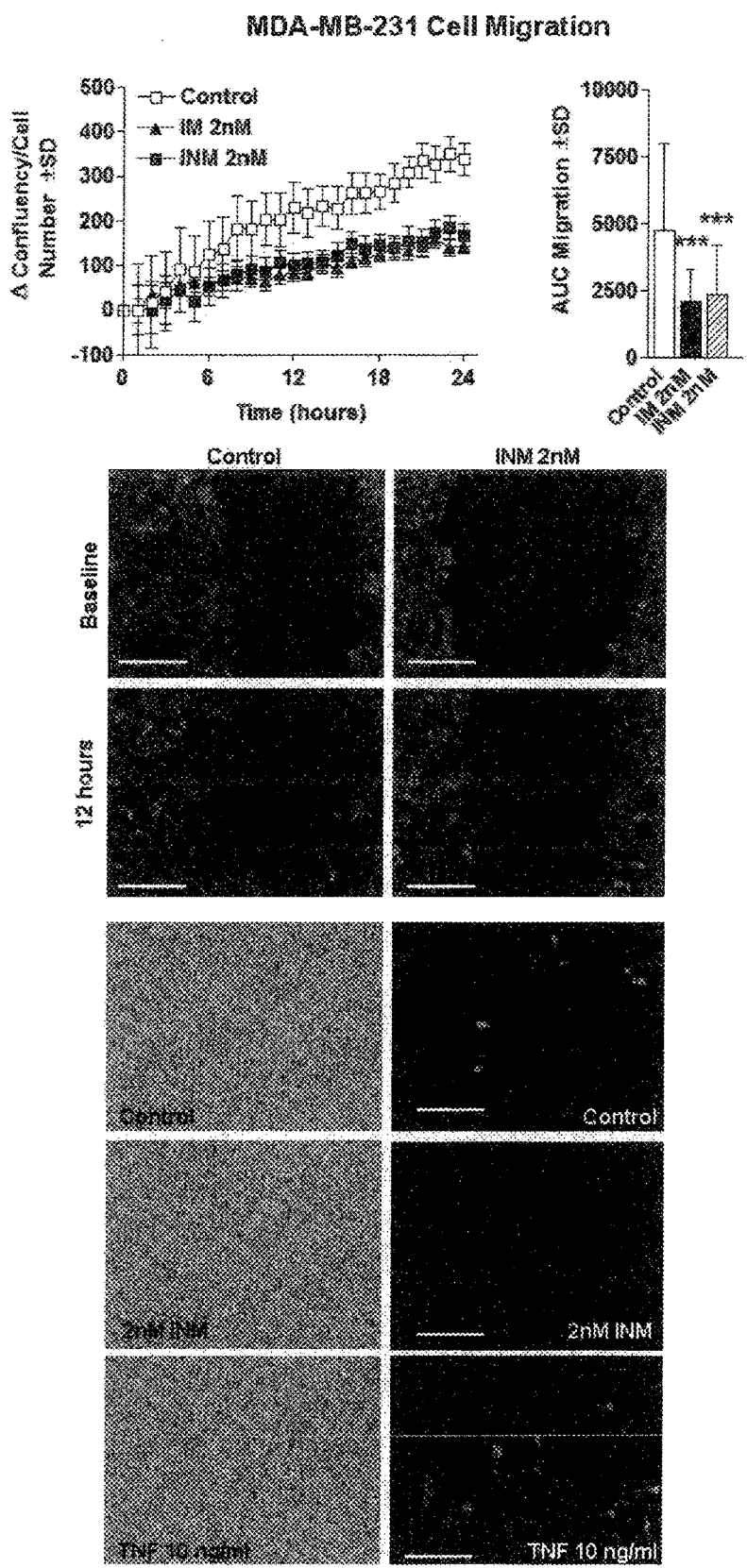

To assess the effects of irisin on breast epithelial cell viability, cell viability was measured 24 hours after treatment with human recombinant non-modified irisin (INM) or human recombinant modified and active (glycosylated) irisin (IM). Non-malignant MCF-10a cell viability was not affected by INM at any concentration 24 hours post treatment, but was decreased at the highest tested dose of IM (Supporting Information FIG. 1). Following similar treatment, malignant MDA-MB-231 cell viability was significantly reduced at concentrations of INM equal to and greater than 2.5 nM, but was unaffected by IM (FIG. 1a). Because INM significantly altered MDA-MB-231 viability, we then measured cell proliferation using a non-lethal dose of both IM and INM in the MDA-MB231 cell line. Consistent with viability findings, INM significantly decreased cell proliferation at 2 nM while IM did not alter cell proliferation. Additionally, INM significantly decreased cell proliferation when compared to IM (FIG. 1b). Moreover, malignant MDA-MB-231 cells treated with either irisin type displayed significantly reduced cell migration compared with the control (FIG. 1c). To determine the effects of INM on other cell lines, these effects were also investigated in the malignant MCF-7 cell line, which were unaffected at all tested concentrations (Supporting Information FIG. 2a).

Apoptosis

Figure 1D:
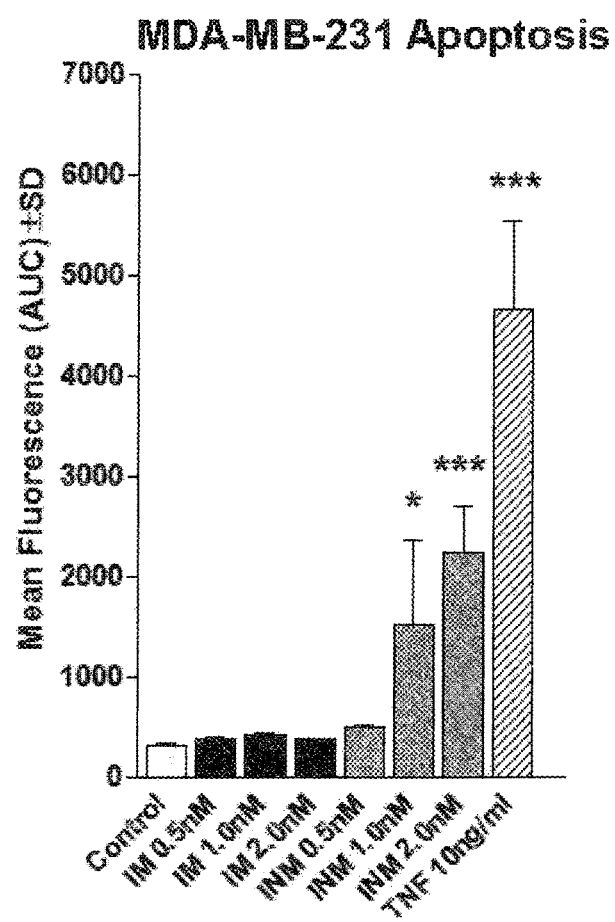
Figure 1E:
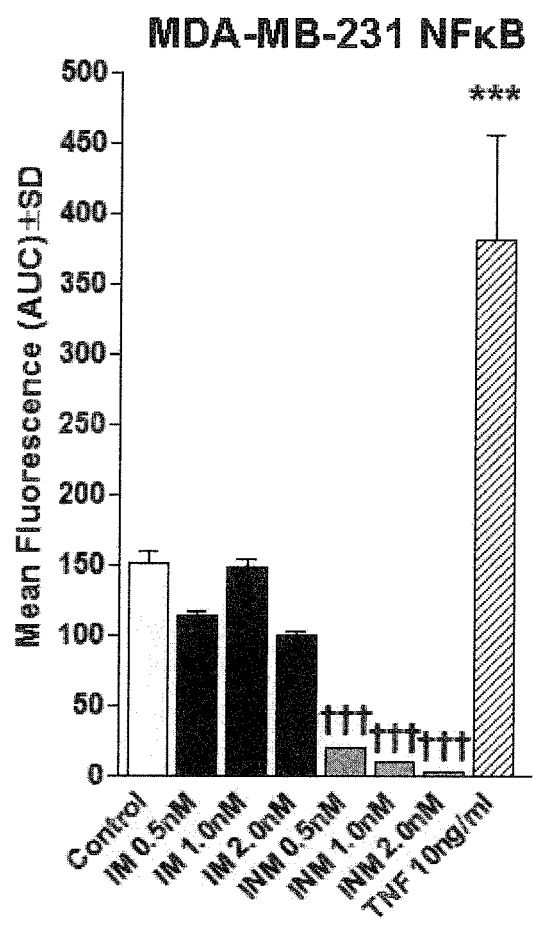
Figure 1F:
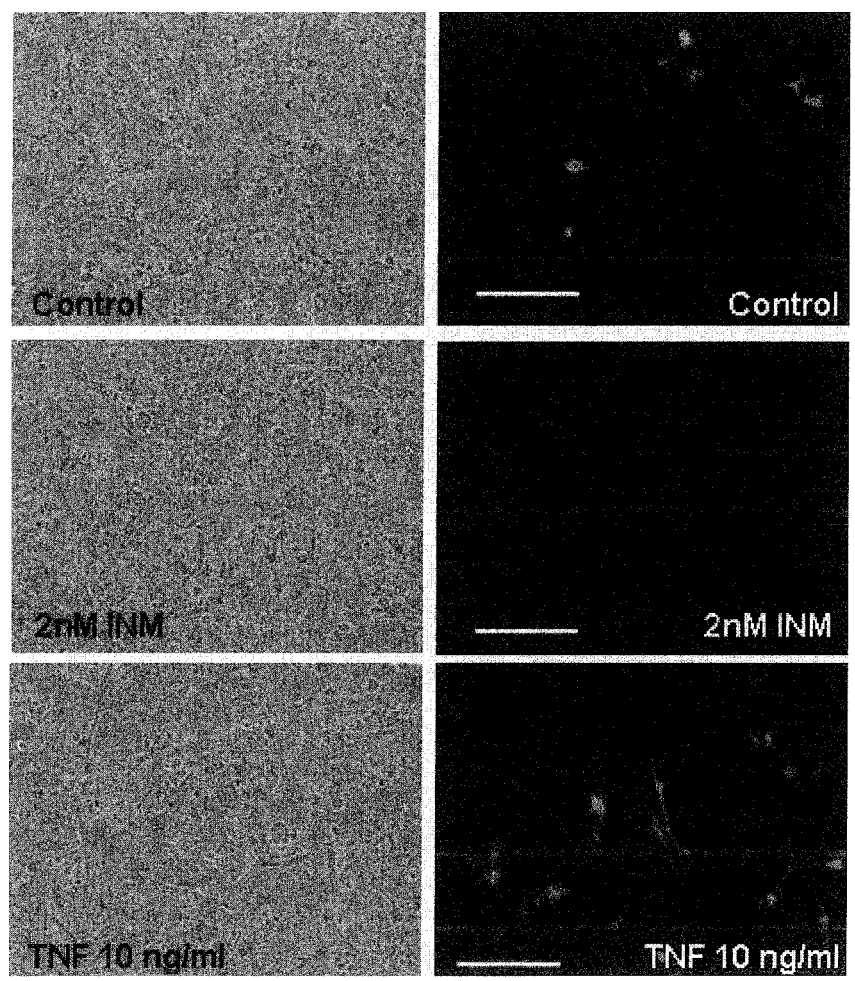

To investigate if the decreased proliferation effects of irisin are due to cell death, we examined irisin-induced apoptosis through activation of caspase-3/7. Malignant MDA-MB-231 cells were treated with various concentrations of INM, IM, and TNF-α (positive control). Caspase-3/7 activity was significantly elevated in cells treated with any dose of INM and TNF-α (FIG. 1d). Conversely, IM failed to activate caspase-3/7 activity at all tested concentrations. Because INM and TNF-α exerted similar effects in malignant breast cells, we measured NFκB activity (a widely accepted pathway activated by TNF-α). While IM did not alter NFκB activity, INM significantly decreased NFκB activity (FIG. 1e).

Doxorubicin Sensitivity

Figure 2A:
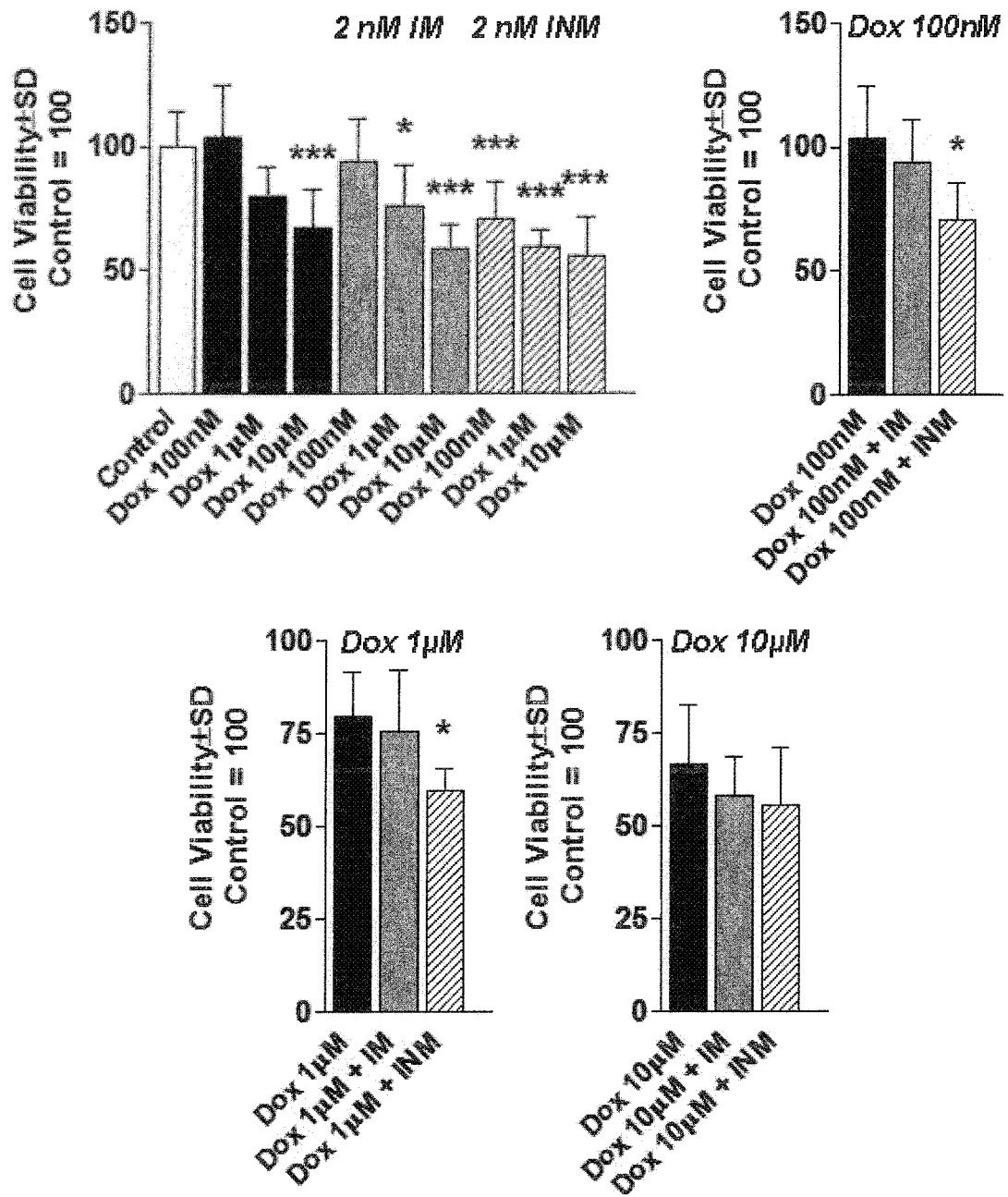
FIG. 2. Doxorubicin Sensitivity. (A) Cell viability of MDA-MB-231 cells treated with control media, or modified irisin (IM) or non-modified irisin (INM) at 2 nM with and without varied Dox (100 nM to 10 μM) for 24 hours. (B) Doxorubicin uptake of MDA-MB-231 cells treated as described above with 2 nM IM or INM and varied Dox indicated by mean fluorescence. (C) Representative images of Dox uptake. (D) Doxorubicin killing efficiency on MDA-MB-231 cells treated as described above represented as a ratio of cell viability to doxorubicin uptake. (E) Cell viability of MDA-MB-231 (left) and MCF-10a (right) cells treated with INM at 2 nM with and without varied Dox (0.156 μM to 10 μM) concentrations. All groups were treated for 24 hours and contain 0.1% DMSO. NOTES: White size bar equals 200 μm. * indicates $P<0.05$ and *** indicates $P<0.001$ compared with control. † indicates $P<0.05$ compared with control or corresponding doxorubicin concentration without INM. As determined in the experiment of Example 1.
Figure 2B:
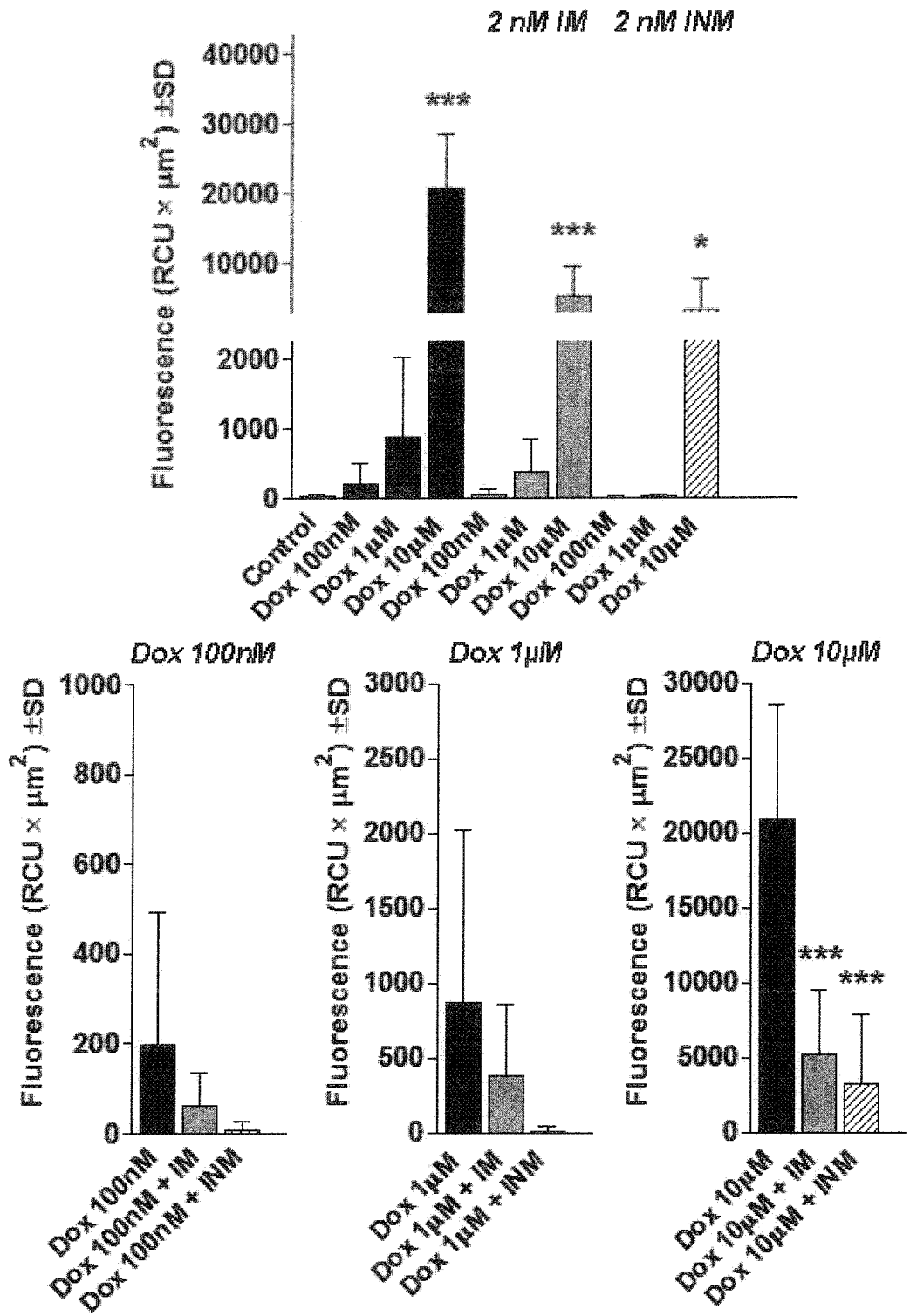
Figure 2C:
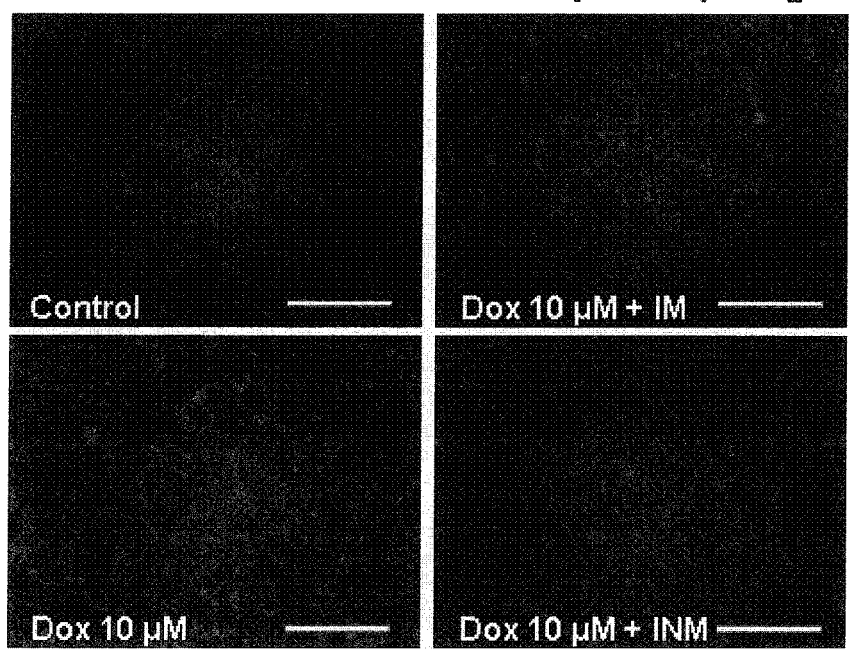
Figure 2D:
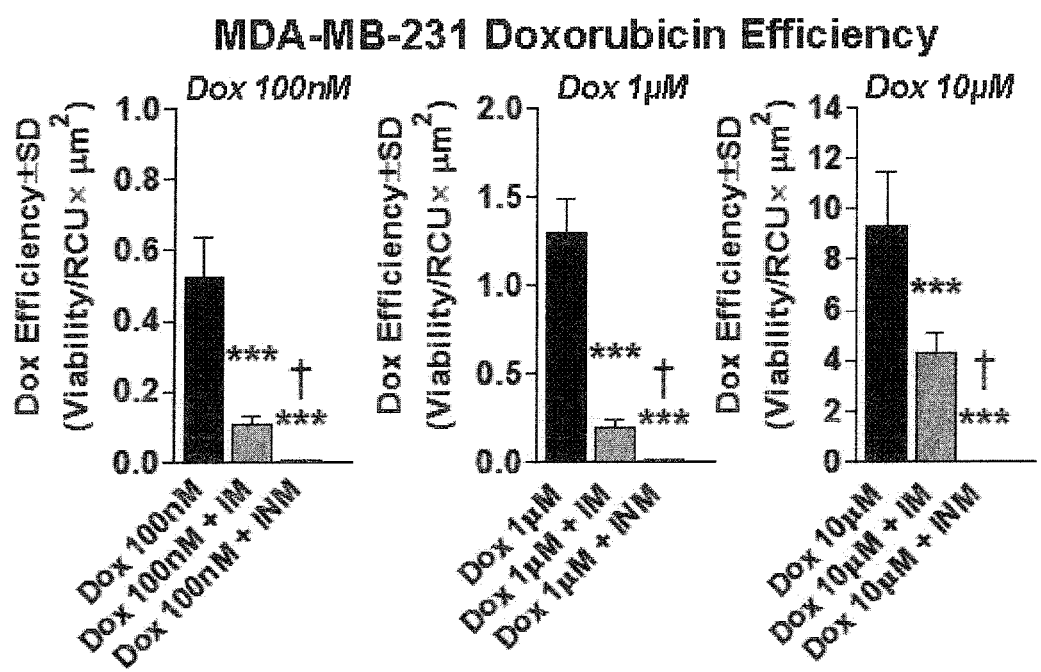
Figure 2E:
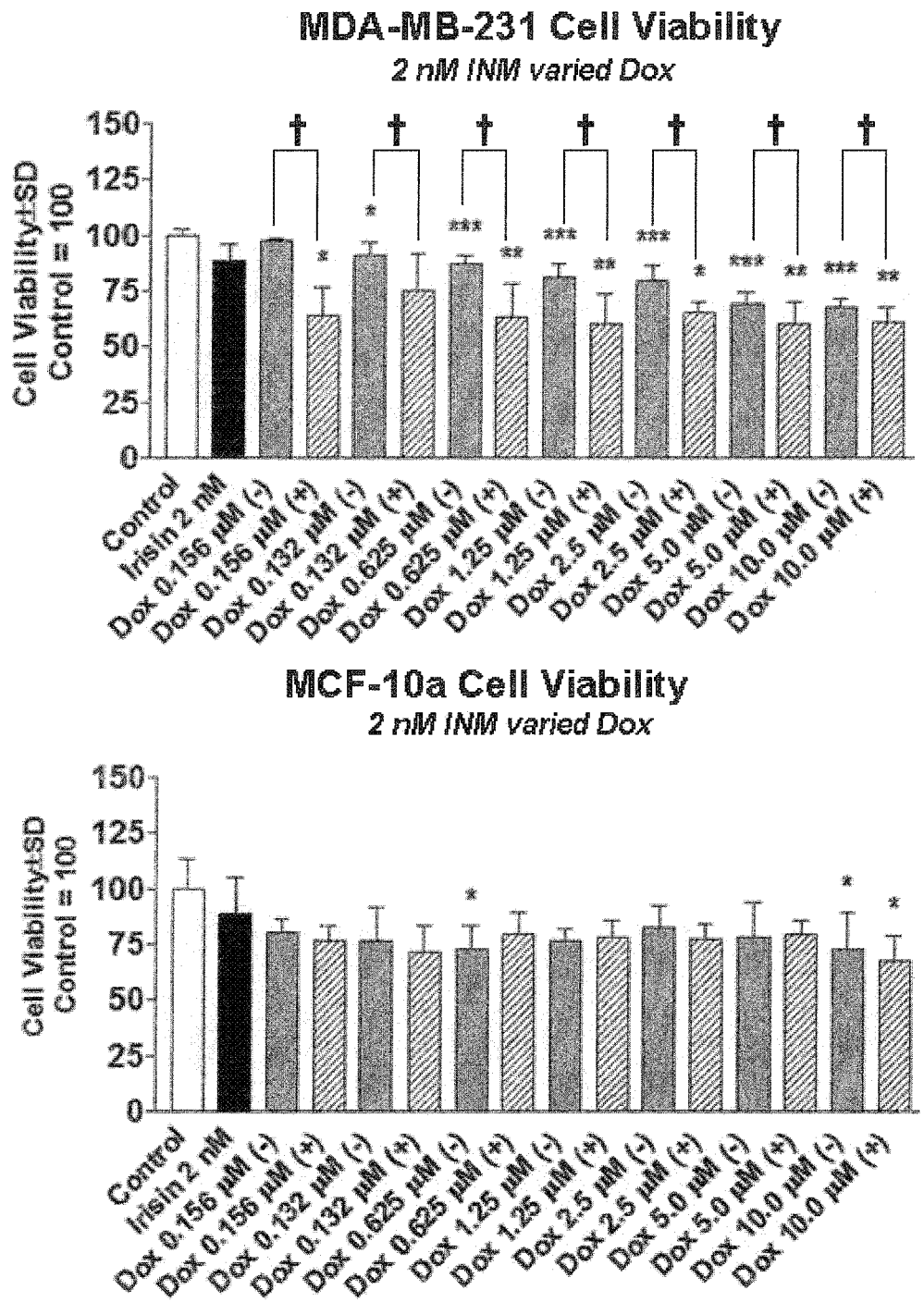

To investigate the effects of irisin on Doxorubicin (Dox)-sensitivity, malignant MDA-MB-231 cells were treated with varying concentrations of Dox with or without 2 nM IM or NM for 24 hours. Dox treatment alone reduced cell viability at 10 µM, but not at 100 nM or 1.0 µM, however IM significantly enhanced Dox killing at 1.0 µM, while INM significantly enhanced Dox killing at all tested concentrations (FIG. 2a). Next we investigated if the synergistic effect between irisin and Dox was a result of increased Dox uptake. Suprisingly, both irisin treatments resulted in decreased Dox uptake (FIG. 2b), suggesting that irisin can function to increase the efficacy of Dox-induced cell death (FIGS. 2c and d) even though less Dox is uptaken by the cell. Lastly, we screened a wide range (0.156 nM-10 µM) of Dox with and without INM to evaluate the limits of irisin enhancement of Dox cytotoxicity. Interestingly INM significantly increased the cytotoxicity of Dox at all tested concentrations (FIG. 2e). And perhaps more interesting was the observation that INM selectively enhanced Dox cytotoxicity in the malignant MCF-7 cells (Supporting Information FIG. 2b), while INM did not enhance Dox cytotoxicity in the non-malignant MCF-10a cells (FIG. 2e).

Discussion

Our data implicate irisin as a potential therapeutic agent for a cancer. Our current findings suggest that irisin has a profound suppressive effect on proliferative and migratory characteristics in malignant breast cancer cells, without affecting non-malignant cells. Furthermore, we demonstrated that irisin induces cell death in malignant breast cells. Last, we demonstrated that irisin has a significant suppressive effect on NFκB activity. This suggests that irisin may have an anti-inflammatory effect, potentially counteracting inflammatory cytokines such as TNF-α.

It appears that post-translational modifications of irisin appear to modify the effects of irisin, although contrary to previous findings, our data support that non-modified irisin may be more effective for suppressing malignant cell viability, proliferation, and migration possibly through apoptosis.[21] Taken together, these observations suggest that irisin may represent a link between exercise and redued incidence of cancer, and that recombinant irisin therapeutics may have direct implications for metastatic disease.[9] We have also demonstrated that non-modified irisin sensitizes malignant MDA-MB-231 and MCF-7 cells to Dox treatment without altering non-malignant cell sensitivity to Dox. Specifically, MDA-MB-231 cells demonstrate greatest irisin-induced increase in sensitivity with viability decreasing to approximately 60-70% of control for all tested concentrations of Dox, while simultaneously decreasing Dox uptake. Although speculative, these data suggest that irisin may allow for reduced doses of common antineoplastics (increased tumor sensitivity) thereby improving patient tolerance and prognosis. Lastly, because irisin has previously been reported to alter cellular metabolism we investigated the effects of irisin on both malignant and non-malignant breast epithelial cell metabolism, which was not significantly altered (data not shown).

Conversely, previous findings by Moon et al. showed that irisin has no significant affect on cell proliferation in obesity-related cancer cells, however these discrepancies may be a function of varied experimental technique or cell type.[16] The predominant technique for assessing proliferation in Moon et al. was an MTT endpoint assay which is an indirect indicator of metabolic potential.[16] Because the MTT assay is measured during a single time point, these observations did not take into account the temporal dynamic of proliferation. In contrast, our measurements encompass constant cell surveillance of fluorescent cell number and confluency, in addition to metabolic endpoint assays.

Conclusion

Exercise has been shown to result in reduced cancer risk and improved prognosis of cancer patients.[22] Our data provides possible insights into potential mechanisms underlying these observations. Moreover, our data supports the hypothesis that irisin may play an important role in future cancer therapeutics, warranting the need for further investigation.

SUPPLEMENTARY TABLE 1

Culture growth media for MCF-10a, MCF-7 and MDA-MB-231 Cells
Abbreviations: Dulbecco's Modified Eagles Medium (DMEM); Fetal Bovine Serum (FBS); pencillin/streptomycin (PS)
All reagents were purchased from Sigma (St. Louis, MO)
Culture Media

| MCF-10a | MCF-7 | MDA-MB-231 |
| --- | --- | --- |
| DMEM/F12 | DMEM | DMEM |
| 5% heat-inactivated FBS | 10% heat-inactivated FBS | 10% heat-inactivated FBS |
| 50 nM hydrocortisone | 0.01 ng/ml human insulin | 100 U/ml (1%) PS |

SUPPLEMENTARY TABLE 1-continued

Culture growth media for MCF-10a, MCF-7 and MDA-MB-231 Cells
Abbreviations: Dulbecco's Modified Eagles Medium (DMEM); Fetal Bovine Serum (FBS); pencillin/streptomycin (PS)
All reagents were purchased from Sigma (St. Louis, MO)
Culture Media

| MCF-10a | MCF-7 | MDA-MB-231 |
| --- | --- | --- |
| 20 ng/ml epidermal growth factor 0.01 ng/ml human insulin 100 UI/ml (1%) PS | 100 UI/ml (1%) PS | |

REFERENCES (FIRST SET)

1. Hanahan D, Weinberg R A. Hallmarks of cancer: the next generation. Cell 2011; 144: 646-74.
2. Warren T Y, Barry V, Hooker S P, Sui X, Church T S, Blair S N. Sedentary behaviors increase risk of cardiovascular disease mortality in men. Med Sci Sports Exerc 2010; 42: 879-85.
3. LaMonte M J, Blair S N, Church T S. Physical activity and diabetes prevention. J Appl Physiol (1985) 2005; 99: 1205-13.
4. Friedenreich C M, Orenstein M R. Physical activity and cancer prevention: etiologic evidence and biological mechanisms. J Nutr 2002; 132: 3456S-64S.
5. Holick C N, Newcomb P A, Trentham-Dietz A, Titus-Ernstoff L, Bersch A J, Stampfer M J, Baron J A, Egan K M, Willett W C. Physical activity and survival after diagnosis of invasive breast cancer. Cancer Epidemiol Biomarkers Prev 2008; 17: 379-86.
6. Loprinzi P D, Cardinal B J, Winters-Stone K, Smit E, Loprinzi C L. Physical activity and the risk of breast cancer recurrence: a literature review. Oncol Nurs Forum 2012; 39: 269-74.
7. Chen X, Lu W, Zheng W, Gu K, Matthews C E, Chen Z, Zheng Y, Shu X O. Exercise after diagnosis of breast cancer in association with survival. Cancer Prev Res (Phila) 2011; 4: 1409-18.
8. Holmes M D, Chen W Y, Feskanich D, Kroenke C H, Colditz G A. Physical activity and survival after breast cancer diagnosis. JAMA 2005; 293: 2479-86.
9. Bostrom P, Wu J, Jedrychowski M P, Korde A, Ye L, Lo J C, Rasbach K A, Bostrom E A, Choi J H, Long J Z, Kajimura S, Zingaretti M C, et al. A PGC1-alpha-dependent myokine that drives brown-fat-like development of white fat and thermogenesis. Nature 2012; 481: 463-U72.
10. Hofmann T, Elbelt U, Ahnis A, Kobelt P, Rose M, Stengel A. Irisin Levels are Not Affected by Physical Activity in Patients with Anorexia Nervosa. Front Endocrinol (Lausanne) 2014; 4: 202.
11. Liu J J, Liu S, Wong M D, Tan C S, Tavintharan S, Sum C F, Lim S C. Relationship between circulating irisin, renal function and body composition in type 2 diabetes. J Diabetes Complications 2014; 28: 208-13.
12. Wen M S, Wang C Y, Lin S L, Hung K C. Decrease in irisin in patients with chronic kidney disease. PLoS One 2013; 8: e64025.
13. Lee P, Linderman J D, Smith S, Brychta R J, Wang J, Idelson C, Perron R M, Werner C D, Phan G Q, Kammula U S, Kebebew E, Pacak K, et al. Irisin and FGF21 are cold-induced endocrine activators of brown fat function in humans. Cell Metab 2014; 19: 302-9.
14. Scharhag-Rosenberger F, Morsch A, Wegmann M, Ruppenthal S, Kaestner L, Meyer T, Hecksteden A. Irisin Does Not Mediate Resistance Training-Induced Alterations in RMR. *Med Sci Sports Exerc* 2014.

15. Vaughan R A, Gannon N P, Barberena M A, Garcia-Smith R, Bisoffi M, Mermier C M, Conn C A, Trujillo K A. Characterization of the metabolic effects of Irisin on skeletal muscle in vitro. *Diabetes Obes Metab* 2014.

16. Moon H S, Mantzoros C S. Regulation of cell proliferation and malignant potential by irisin in endometrial, colon, thyroid and esophageal cancer cell lines. *Metabolism* 2013.

17. Vaughan R A, Garcia-Smith R, Dorsey J, Griffith J K, Bisoffi M, Trujillo K A. Tumor necrosis factor alpha induces Warburg-like metabolism and is reversed by anti-inflammatory curcumin in breast epithelial cells. *Int J Cancer* 2013; 133: 2504-10.

18. Sansone P, Storci G, Tavolari S, Guarnieri T, Giovannini C, Taffurelli M, Ceccarelli C, Santini D, Paterini P, Marcu K B, Chieco P, Bonafe M. IL-6 triggers malignant features in mammospheres from human ductal breast carcinoma and normal mammary gland. *J Clin Invest* 2007; 117: 3988-4002.

19. Madeleine M M, Johnson L G, Malkki M, Resler A J, Petersdorf E W, McKnight B, Malone K E. Genetic variation in proinflammatory cytokines IL6, IL6R, TNF-region, and TNFRSF1A and risk of breast cancer. *Breast Cancer Res Treat* 2011; 129: 887-99.

20. Wu G S, Lu J J, Guo J J, Huang M Q, Gan L, Chen X P, Wang Y T. Synergistic anti-cancer activity of the combination of dihydroartemisinin and doxorubicin in breast cancer cells. *Pharmacol Rep* 2013; 65: 453-9.

21. Zhang Y, Li R, Meng Y, Li S, Donelan W, Zhao Y, Qi L, Zhang M, Wang X, Cui T, Yang L J, Tang D. Irisin stimulates browning of white adipocytes through mitogen-activated protein kinase p38 MAP kinase and ERK MAP kinase signaling. *Diabetes* 2014; 63: 514-25.

22. Hojman P, Dethlefsen C, Brandt C, Hansen J, Pedersen L, Pedersen B K. Exercise-induced muscle-derived cytokines inhibit mammary cancer cell growth. *Am J Physiol Endocrinol Metab* 2011; 301: E504-10.

EXAMPLE 2

Effect of Irisin on Prostate Cancer

Materials and Methods

Cell culture and Treatments—Human pre-malignant and non-tumorigenic RWPE-1, tumorigenic and non-aggressive LNCaP (androgen sensitive), tumorigenic and aggressive DU145 (androgen insensitive), and tumorigenic and highly aggressive PC-3 (androgen insensitive) were purchased from American Type Culture Collection (Manassas, Va.) and maintained under standard conditions (37° C. in 5% $CO_2$). RWPE-1 cells were cultured in serum-free keratinocyte medium from Invitrogen (Carlsbad, Calif.) and supplemented with 25 ng/ml epidermal growth factor (EGF), 25 mg/ml bovine pituitary extract, 5 mM L-glutamine, 1% heat-inactivated FBS, and 100 U/ml penicillin/streptomycin; LNCaP, DU145, and PC-3 cells were cultured in RPMI-1640 medium from Invitrogen and supplemented with 5 mM L-glutamine, 10% FBS, and 100 U/ml penicillin/streptomycin. Cell lines were labeled with red fluorescent protein (RFP) by lentiviral-transfection using NucLight Red from Essen Bioscience (Ann Arbor, Mich.). Successfully transfected cells were selected using media containing 1 µg/ml puromycin and thereafter cultured in media containing 0.5 µg/ml puromycin, as previously described (22). Cells were treated with human recombinant non-modified irisin (INM) (lacking post-translational glycosylation) from Cayman Chemical (Ann Arbor, Mich.) at concentrations ranging from 0.625 nM to 20 nM dissolved in culture media or culture media control for up to 24 hours. Doses of irisin were determined through pilot data and previous observations (9,12,22).

Cell proliferation and migration—Cells were seeded overnight at a density of 5,000 cells/well and treated with or without INM. Cell proliferation was measured by automated red object counting optimized for each respective cell type using the Incucyte ZOOM live content imaging from Essen Bioscience (Ann Arbor, Mich.). Cell migration was assessed after applying a scratch through confluent cells cultured in a 96-well plate. Confluent cells were treated with or without 2 nM and 20 nM INM 24 hours prior to scratch. The cells were then rinsed and the media replaced with corresponding treatment. Migration was indicated by change in well confluence (confluence-mask quantification via Incucyte ZOOM phase-contrast) normalized to cell number.

Cell viability, docetaxel cytotoxicity, and androgen sensitivity—Cells were seeded overnight at a density of 5,000 cells/well, and treated with and without varying concentrations of INM for 24 hours. Cells were then incubated for 1 hour in medium containing 10% WST-1 cell proliferation reagent from Roche (Indianapolis, Ind.) and fluorescence was measured using a Wallac Victor3V 1420 Multilabel Counter from PerkinElmer (Waltham, Mass.). These methods were repeated with varying concentrations (from 2 nM to 40 nM) of the anti-mitotic chemotherapy docetaxel (Doc) (in DMSO using 0.1% for all treatments including control) from Sigma (St. Louis, Mo.) with and without varying concentrations of irisin for 24 hours. PC3 and DU145 cells were co-incubated with INM and R1881 synthetic androgen and testosterone analog for 24 hours (1 nM and 10 nM) from Sigma (St. Louis, Mo.) in phenol red-free RPMI, containing 10% charcoal-stripped FBS from Sigma (St. Louis, Mo.). Treatment doses and durations were determined through pilot data for irisin and from previous observations for Doc and R1881 (23-29).

NFκB-GFP Reporter System

Cells were transfected with a NFκB GFP-linked reporter system from Qiagen (Valencia, Calif.) before treatment with INM or TNF-α from R and D Systems (Minneapolis, Minn.) at various concentrations for 24 hours. NFκB activity was indicated by mean fluorescence measured by the Incucyte ZOOM as described above.

Caspase-3/7 Activity

Cells were co-treated as previously described (N=12) with a kinetic caspase-3/7 apoptosis reagent from Essen Bioscience (Ann Arbor, Mich.). Caspase-3/7 activity was indicated by mean green fluorescence measured by the Incucyte ZOOM as described above.

Statistical Analyses

Data was analyzed using one-way ANOVA with Dunnett's or two-way ANOVA Bonferroni's post hoc pairwise comparisons. All data is represented as average±standard deviation with values of p<0.05 indicating statistical significance.

Results

Proliferation and Viability

To assess the effects of INM on prostate epithelial cell proliferation, cells were treated for 24 hours with and without INM. INM significantly suppressed PC3 cell proliferation at all concentrations, beginning as early as 6 hours post-treatment (FIG. 1A). And consistent with these findings, LNCaP cells treated with INM demonstrated significantly decreased cell proliferation at all concentrations, with the exception of 10 nM, as early as 9 hours following treatment (FIG. 1B). The slowing influence INM appears to have on the other tumorigenic cell lines tested was not as profoundly seen in DU145 cells, as cell proliferation was only significantly decreased following treatment of INM at 20 nM, (FIG. 6C). Non-malignant RWPE-1 cell proliferation was not altered by any tested concentrations of INM (FIG. 6D).

INM did not negatively affect cell viability of any cell type used (FIGS. 7A, B, C, and E). Therefore, because INM appears to have a suppressive effect on tumorigenic prostate epithelial cell proliferation, without altering cell viability at analogous concentrations, we choose to proceed with further analyses using INM at both 2 nM (physiologically relevant) and 20 nM (pharmaceutically relevant).

The results presented in Example 2 evidence that Irisin has significant potential as an anti-prostate cancer composition for use in the treatment and/or prevention of prostate cancer as otherwise described herein.

REFERENCES (SECOND SET) SECOND SECTION OF INTRODUCTION AND EXAMPLE 2

1. Bianchini F, Kaaks R, Vainio H. Overweight, obesity, and cancer risk. Lancet Oncol 2002; 3(9):565-574.
2. Calle E E, Rodriguez C, Walker-Thurmond K, Thun M J. Overweight, obesity, and mortality from cancer in a prospectively studied cohort of U.S. adults. N Engl J Med 2003; 348(17):1625-1638.
3. Calle E E, Kaaks R. Overweight, obesity and cancer: epidemiological evidence and proposed mechanisms. Nat Rev Cancer 2004; 4(8):579-591.
4. Cuzick J, Thorat M A, Andriole G, Brawley O W, Brown P H, Culig Z, Eeles R A, Ford L G, Hamdy F C, Holmberg L, Ilic D, Key T J, La Vecchia C, Lilja H, Marberger M, Meyskens F L, Minasian L M, Parker C, Parnes H L, Perner S, Rittenhouse H, Schalken J, Schmid H P, Schmitz-Dräger B J, Schröder F H, Stenzl A, Tombal B, Wilt T J, Wolk A. Prevention and early detection of prostate cancer. Lancet Oncol 2014; 15(11):e484-492.
5. Davies N J, Batehup L, Thomas R. The role of diet and physical activity in breast, colorectal, and prostate cancer survivorship: a review of the literature. Br J Cancer 2011; 105 Suppl 1:S52-73.
6. Gong Z, Neuhouser M L, Goodman P J, Albanes D, Chi C, Hsing A W, Lippman S M, Platz E A, Pollak M N, Thompson I M, Kristal A R. Obesity, diabetes, and risk of prostate cancer: results from the prostate cancer prevention trial. Cancer Epidemiol Biomarkers Prev 2006; 15(10):1977-1983.
7. Kenfield S A, Stampfer M J, Giovannucci E, Chan J M. Physical activity and survival after prostate cancer diagnosis in the health professionals follow-up study. J Clin Oncol 2011; 29(6):726-732.
8. Richman E L, Kenfield S A, Stampfer M J, Paciorek A, Carroll P R, Chan J M. Physical activity after diagnosis and risk of prostate cancer progression: data from the cancer of the prostate strategic urologic research endeavor. Cancer Res 2011; 71(11):3889-3895.
9. Bostrom P, Wu J, Jedrychowski M P, Korde A, Ye L, Lo J C, Rasbach K A, Bostrom E A, Choi J H, Long J Z, Kajimura S, Zingaretti M C, Vind B F, Tu H, Cinti S, Hojlund K, Gygi S P, Spiegelman B M. A PGC1-alpha-dependent myokine that drives brown-fat-like development of white fat and thermogenesis. Nature 2012; 481 (7382):463-U472.
10. Schumacher M A, Chinnam N, Ohashi T, Shah R S, Erickson H P. The structure of irisin reveals a novel intersubunit β-sheet fibronectin type III (FNIII) dimer: implications for receptor activation. J Biol Chem 2013; 288(47):33738-33744.
11. Zhang Y, Li R, Meng Y, Li S, Donelan W, Zhao Y, Qi L, Zhang M, Wang X, Cui T, Yang L J, Tang D. Irisin stimulates browning of white adipocytes through mitogen-activated protein kinase p38 MAP kinase and ERK MAP kinase signaling. Diabetes 2014; 63(2):514-525.
12. Vaughan R A, Gannon N P, Barberena M A, Garcia-Smith R, Bisoffi M, Mermier C M, Conn C A, Trujillo K A. Characterization of the metabolic effects of irisin on skeletal muscle in vitro. Diabetes Obes Metab 2014.
13. Löffler D, Müller U, Scheuermann K, Friebe D, Gesing J, Bielitz J, Erbs S, Landgraf K, Viola Wagner I, Kiess W, Körner A. Serum irisin levels are regulated by acute strenuous exercise. J Clin Endocrinol Metab 2015: jc20142932.
14. Norheim F, Langleite T M, Hjorth M, Holen T, Kielland A, Stadheim H K, Gulseth H L, Birkeland K I, Jensen J, Drevon C A. The effects of acute and chronic exercise on PGC-1α, irisin and browning of subcutaneous adipose tissue in humans. FEBS J 2014; 281(3):739-749.
15. Huh J Y, Mougios V, Kabasakalis A, Fatouros I, Siopi A, Douroudos I I, Filippaios A, Panagiotou G, Park K H, Mantzoros C S. Exercise-induced irisin secretion is independent of age or fitness level and increased irisin may directly modulate muscle metabolism through AMPK activation. J Clin Endocrinol Metab 2014; 99(11):E2154-2161.
16. Zhang C, Ding Z, Lv G, Li J, Zhou P, Zhang J. Lower Irisin Level in Patients with Type 2 Diabetes Mellitus: a Case-control Study and Meta-analysis. J Diabetes 2014.
17. Zhang M, Chen P, Chen S, Sun Q, Zeng Q C, Chen J Y, Liu Y X, Cao X H, Ren M, Wang J K. The association of new inflammatory markers with type 2 diabetes mellitus and macrovascular complications: a preliminary study. Eur Rev Med Pharmacol Sci 2014; 18(11):1567-1572.
18. Liu J J, Liu S, Wong M D, Tan C S, Tavintharan S, Sum C F, Lim S C. Relationship between circulating irisin, renal function and body composition in type 2 diabetes. J Diabetes Complications 2014; 28(2):208-213.
19. Park K H, Zaichenko L, Brinkoetter M, Thakkar B, Sahin-Efe A, Joung K E, Tsoukas M A, Geladari E V, Huh J Y, Dincer F, Davis C R, Crowell J A, Mantzoros C S. Circulating irisin in relation to insulin resistance and the metabolic syndrome. J Clin Endocrinol Metab 2013; 98(12):4899-4907.
20. Yan B, Shi X, Zhang H, Pan L, Ma Z, Liu S, Liu Y, Li X, Yang S, Li Z. Association of serum irisin with metabolic syndrome in obese Chinese adults. PLoS One 2014; 9(4):e94235.
21. Pardo M, Crujeiras A B, Amil M, Aguera Z, Jiménez-Murcia S, Baños R, Botella C, de la Torre R, Estivill X, Fagundo A B, Fernández-Real J M, Fernández-García J C, Fruhbeck G, Gómez-Ambrosi J, Rodríguez R, Tinahones F J, Fernández-Aranda F, Casanueva F F. Association of irisin with fat mass, resting energy expenditure, and daily activity in conditions of extreme body mass index. Int J Endocrinol 2014; 2014:857270.
22. Gannon N P, Vaughan R A, Garcia-Smith R, Bisoffi M, Trujillo K A. Effects of the exercise-inducible myokine irisin on malignant and non-malignant breast epithelial cell behavior in vitro. Int J Cancer 2014.
23. Mimeault M, Johansson S L, Batra S K. Marked improvement of cytotoxic effects induced by docetaxel on highly metastatic and androgen-independent prostate cancer cells by downregulating macrophage inhibitory cytokine-1. Br J Cancer 2013; 108(5):1079-1091.
24. Mimeault M, Johansson S L, Vankatraman G, Moore E, Henichart J P, Depreux P, Lin M F, Batra S K. Combined targeting of epidermal growth factor receptor and hedgehog signaling by gefitinib and cyclopamine cooperatively improves the cytotoxic effects of docetaxel on metastatic prostate cancer cells. Mol Cancer Ther 2007; 6(3):967-978.
25. Tamaki H, Harashima N, Hiraki M, Arichi N, Nishimura N, Shiina H, Naora K, Harada M. Bcl-2 family inhibition sensitizes human prostate cancer cells to docetaxel and promotes unexpected apoptosis under caspase-9 inhibition. Oncotarget 2014; 5(22):11399-11412.
26. Festuccia C, Gravina G L, D'Alessandro A M, Muzi P, Millimaggi D, Dolo V, Ricevuto E, Vicentini C, Bologna M. Azacitidine improves antitumor effects of docetaxel and cisplatin in aggressive prostate cancer models. Endocr Relat Cancer 2009; 16(2):401-413.
27. Cao P, Deng Z, Wan M, Huang W, Cramer S D, Xu J, Lei M, Sui G. MicroRNA-101 negatively regulates Ezh2 and its expression is modulated by androgen receptor and HIF-1alpha/HIF-1beta. Mol Cancer 2010; 9:108.
28. Lee C M, Yen C H, Tzeng T Y, Huang Y Z, Chou K H, Chang T J, Arthur Chen Y M. Androgen response element of the glycine N-methyltransferase gene is located in the coding region of its first exon. Biosci Rep 2013; 33(5).
29. Xi Z, Klokk T I, Korkmaz K, Kurys P, Elbi C, Risberg B, Danielsen H, Loda M, Saatcioglu F. Kallikrein 4 is a predominantly nuclear protein and is overexpressed in prostate cancer. Cancer Res 2004; 64(7):2365-2370.

What is claimed is:

1. A method of treating a subject who suffers from prostate or breast cancer, the method comprising administering to the subject a composition comprising a therapeutically effective amount of irisin, wherein said irisin is a polypeptide consisting of the sequence SEQ ID NO: 1, or the sequence SEQ ID NO: 2, or a glycosylated form of said polypeptide of SEQ ID NO: 1 or SEQ ID NO: 2, or a pharmaceutically acceptable salt thereof.

2. The method according to claim 1 wherein said irisin is a polypeptide consisting of SEQ ID NO:1 , or a pharmaceutically acceptable salt thereof.

3. The method according to claim 1 wherein said irisin is a polypeptide consisting of SEQ ID NO: 2, or a pharmaceutically acceptable salt thereof.

4. The method according to claim 1 wherein said cancer is breast cancer.

5. The method according to claim 1 wherein said cancer is refractory breast cancer.

6. The method according to claim 1 wherein said cancer is recurrent breast cancer.

7. The method according to claim 1 wherein said breast cancer is drug resistant breast cancer.

8. The method according to claim 1 wherein said breast cancer is metastatic breast cancer.

9. The method according to claim 1 wherein said breast cancer has developed an acquired anti-estrogen resistance.

10. The method according to claim 1 wherein said breast cancer has developed an acquired anti-estrogen resistance.

11. The method according to claim 1 wherein said cancer is breast cancer and the subject exhibits an intrinsic resistance to anti-estrogen and anti-HER2 therapies.

12. The method according to claim 1 wherein said composition further includes doxorubicin, daunorubicin or a pharmaceutically acceptable salt thereof.

13. The method according to claim 2 wherein said composition further includes doxorubicin, daunorubicin or a pharmaceutically acceptable salt thereof.

14. The method according to claim 3 wherein said composition further includes doxorubicin, daunorubicin or a pharmaceutically acceptable salt thereof.

15. The method according to claim 4 wherein said composition further includes doxorubicin, daunorubicin or a pharmaceutically acceptable salt thereof.

16. The method according to claim 5 wherein said composition further includes doxorubicin, daunorubicin or a pharmaceutically acceptable salt thereof.

17. The method according to claim 1 wherein said method comprises co-administering doxorubicin, daunorubicin or a pharmaceutically acceptable salt thereof to said subject.

18. The method according to claim 2 wherein said method comprises co-administering doxorubicin, daunorubicin or a pharmaceutically acceptable salt thereof to said subject.

19. The method according to claim 3 wherein said method comprises co-administering doxorubicin, daunorubicin or a pharmaceutically acceptable salt thereof to said subject.

20. The method according to claim 4 wherein said method comprises co-administering doxorubicin, daunorubicin or a pharmaceutically acceptable salt thereof to said subject.

21. The method according to claim 5 wherein said method comprises co-administering doxorubicin, daunorubicin or a pharmaceutically acceptable salt thereof to said subject.

22. The method according to claim 1 wherein said composition further includes doxorubicin or a pharmaceutically acceptable salt thereof.

23. The method according to claim 2 wherein said composition further includes doxorubicin or a pharmaceutically acceptable salt thereof.

24. The method according to claim 3 wherein said composition further includes doxorubicin or a pharmaceutically acceptable salt thereof.

25. The method according to claim 4 wherein said composition further includes doxorubicin or a pharmaceutically acceptable salt thereof.

26. The method according to claim 5 wherein said composition further includes doxorubicin or a pharmaceutically acceptable salt thereof.

27. The method according to claim 1 wherein said method comprises co-administering doxorubicin or a pharmaceutically acceptable salt thereof to said subject.

28. The method according to claim 2 wherein said method comprises co-administering doxorubicin or a pharmaceutically acceptable salt thereof to said subject.

29. The method according to claim 3 wherein said method comprises co-administering doxorubicin or a pharmaceutically acceptable salt thereof to said subject.

30. The method according to claim 4 wherein said method comprises co-administering doxorubicin or a pharmaceutically acceptable salt thereof to said subject.

31. The method according to claim 5 wherein said method comprises co-administering doxorubicin or a pharmaceutically acceptable salt thereof to said subject.

* * * * *

SEQUENCE LISTING

```
<160> NUMBER OF SEQ ID NOS: 3

<210> SEQ ID NO 1
<211> LENGTH: 112
<212> TYPE: PRT
<213> ORGANISM: Artificial
<220> FEATURE:
<223> OTHER INFORMATION: non-modified irisin

<400> SEQUENCE: 1

Asp Ser Pro Ser Ala Pro Val Asn Val Thr Val Arg His Leu Lys Ala
1               5                   10                  15

Asn Ser Ala Val Val Ser Trp Asp Val Leu Glu Asp Glu Val Val Ile
            20                  25                  30

Gly Phe Ala Ile Ser Gln Gln Lys Lys Asp Val Arg Met Leu Arg Phe
        35                  40                  45

Ile Gln Glu Val Asn Thr Thr Thr Arg Ser Cys Ala Leu Trp Asp Leu
    50                  55                  60

Glu Glu Asp Thr Glu Gly Ile Val His Val Gln Ala Ile Ser Ile Gln
65                  70                  75                  80

Gly Gln Ser Pro Ala Ser Glu Pro Val Leu Phe Lys Thr Pro Arg Glu
                85                  90                  95

Ala Glu Lys Met Ala Ser Lys Asn Lys Asp Glu Val Thr Met Lys Glu
            100                 105                 110

<210> SEQ ID NO 2
<211> LENGTH: 111
<212> TYPE: PRT
<213> ORGANISM: Artificial
<220> FEATURE:
<223> OTHER INFORMATION: non-modified irisin variant

<400> SEQUENCE: 2

Ser Pro Ser Ala Pro Val Asn Val Thr Val Arg His Leu Lys Ala Asn
1               5                   10                  15

Ser Ala Val Val Ser Trp Asp Val Leu Glu Asp Glu Val Val Ile Gly
            20                  25                  30

Phe Ala Ile Ser Gln Gln Lys Lys Asp Val Arg Met Leu Arg Phe Ile
        35                  40                  45

Gln Glu Val Asn Thr Thr Thr Arg Ser Cys Ala Leu Trp Asp Leu Glu
    50                  55                  60

Glu Asp Thr Glu Gly Ile Val His Val Gln Ala Ile Ser Ile Gln Glu
65                  70                  75                  80
```

```
Gln Ser Pro Ala Ser Glu Pro Val Leu Phe Lys Thr Pro Arg Glu Ala
                85                  90                  95

Glu Lys Met Ala Ser Lys Asn Lys Asp Glu Val Thr Met Lys Glu
            100                 105                 110

<210> SEQ ID NO 3
<211> LENGTH: 117
<212> TYPE: PRT
<213> ORGANISM: Artificial
<220> FEATURE:
<223> OTHER INFORMATION: aegss irisin polypeptide

<400> SEQUENCE: 3

Ala Glu Gly Ser Ser Asp Ser Pro Ser Ala Pro Val Asn Val Thr Val
1               5                   10                  15

Arg His Leu Lys Ala Asn Ser Ala Val Val Ser Trp Asp Val Leu Glu
                20                  25                  30

Asp Glu Val Val Ile Gly Phe Ala Ile Ser Gln Gln Lys Lys Asp Val
            35                  40                  45

Arg Met Leu Arg Phe Ile Gln Glu Val Asn Thr Thr Thr Arg Ser Cys
        50                  55                  60

Ala Leu Trp Asp Leu Glu Glu Asp Thr Glu Tyr Ile Val His Val Gln
65                  70                  75                  80

Ala Ile Ser Ile Gln Gly Gln Ser Pro Ala Ser Glu Pro Val Leu Phe
                85                  90                  95

Lys Thr Pro Arg Glu Ala Glu Lys Met Ala Ser Lys Asn Lys Asp Glu
            100                 105                 110

Val Thr Met Lys Glu
            115
```